US006548742B2

(12) United States Patent
Martin et al.

(10) Patent No.: US 6,548,742 B2
(45) Date of Patent: Apr. 15, 2003

(54) DEVELOPMENT OF RESISTANCE TO RASPBERRY BUSHY DWARF VIRUS

(75) Inventors: Robert R. Martin, Corvallis, OR (US); Helena Mathews, Portland, OR (US); Karen Keller, Shedd, OR (US); Jill A. Kellogg, Bend, OR (US); Ry Wagner, Eugene, OR (US)

(73) Assignees: Exelixis, Inc., South San Francisco, CA (US); The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 09/784,508

(22) Filed: Feb. 14, 2001

(65) Prior Publication Data

US 2002/0046417 A1 Apr. 18, 2002

Related U.S. Application Data

(63) Continuation-in-part of application No. 09/737,719, filed on Dec. 15, 2000.

(60) Provisional application No. 60/171,018, filed on Dec. 15, 1999.

(51) Int. Cl.[7] ........................ C12N 15/82; C12N 15/33; C12N 15/90; C12N 5/04; A01H 5/00

(52) U.S. Cl. .................... 800/280; 435/320.1; 435/419; 435/468; 536/23.72; 800/301

(58) Field of Search ............................ 435/69.1, 320.1, 435/410, 419, 468; 536/23.72; 800/278, 279, 280, 295, 298, 301

(56) References Cited

U.S. PATENT DOCUMENTS 5,898,097 A 4/1999 Beachy et al. .............. 800/279

OTHER PUBLICATIONS

Mathews et al, "Efficient genetic transformation of red raspberry, *Rubus Ideaus* L.", 1995, Plant Cell Reports, vol. 14 pp. 471–476.*

Genbank Accession No. P23629 Raspberry bushy dwarf virus (RBDV), 1995.

EMBL Accession No. Q86563 Raspberry bushy dwarf virus (RBDV), 1998.

EMBL Accession No. Q86564 Raspberry bushy dwarf virus (RBDV), 1998.

Mayo, M.A., et al., "Nucleotide sequence of raspberry bushy dwarf virus RNA–3", *Journal of General Virology, 72*:469–472, 1991.

Beachy, R.N., et al., "Coat protein–mediated resistance against virus infection", *Annu. Rev. Phytopathol.,* 28:451–474, 1990.

Daubney, H.A., et al., "Effects of Raspberry Bushy Dwarf Virus on Yield and Cane Growht in Susceptible Red Raspberry Cultivars" *Hortscience 17*(4):645–647 (1982).

Genbank Accession No. D01052 Raspberry bushy dwarf virus mRNA for coat protein, complet cds. 1999.

Genbank Accession No. S51557 RNA–1 segment: non–structural polyprotein [raspberry bushy dwarf virus RBDV, R15, Genomic RNA Complete, 5449 nt]. 1993.

Genbank Accession No. S55890 RNA–3 coat protein homolog, alfalfa mosaic virus RNA–3 32k protein homolog {RNA–2}. 1993.

Martin, R.R., "Raspberry viruses in Oregon, Washington and British Columbia" *Proc. 8th Int. Symp on Small Fruit Virus Disease, Acta Hortic. 471*:71–74 (1998).

Natsuaki, T., et al., "Nucleotide sequence of raspberry bushy dwarf virus RNA–2: a bicistronic component of a bipartite genome" *Journal of General Virology 72*:2183–2189 (1991).

* cited by examiner

*Primary Examiner*—Amy J. Nelson
*Assistant Examiner*—Ashwin Mehta
(74) *Attorney, Agent, or Firm*—Perkins Coie LLP

(57) ABSTRACT

The present invention relates to isolated Raspberry Bushy Dwarf Virus (RBDV) nucleic acid sequences which encode RBDV coat and movement proteins or polypeptides and mutant or modified forms thereof. The invention further relates to heterologous nucleic acid constructs, vectors, transformation methods, plant cells and plants comprising such RBDV-encoding nucleic acids and methods for inducing resistance to RBDV by transforming plants with a nucleic acid construct comprising RBDV protein or polypeptide-encoding nucleic acid sequences.

7 Claims, 6 Drawing Sheets

ATGGCGAAGAAAGCTGTTCCACCAATCGTTAAGGCTCAATATGAGCTTTATAATCGTAA
GTTGAACAGAGCCATCAAGGTTTCCGGCAGTCAGAAGAAGCTAGACGCTTCTTTTGTCG
GGTTCAGTGAGAGCTCTAACCCAGAAACTGGGAAACCTCACGCGGACATGTCTATGTCT
GCTAAGGTTAAGCGCGTCAATACGTGGCTTAAAAACTTTGATCGCGAATATTGGGATAA
CCAGTTCGCATCAAAACCCGTTCCTAGACCTGCAAAACAGGCCTTGAAGGGTTCATCCT
CCAAACCTCAACAACGAGATGAAGGAGAGGTGGTCTTTACCCGAAAAGACTCCCAGAAA
TCCGTTAGGACTGTGTCCTATTGGGTTTGTACTCCTGAGAAGTCGATGAAACCTCTCAA
ATATAAGGAGGACGAAAACGTCGTTGAAGTTACCTTCAATGACCTCACAGCTCAAAAGG
CTGGTGACAAATTGGTTTCCATTCTGTTGGAAATCAATGTGGTGGGCGGTGCCGTCGAC
GATAAAGGTCGAGTGGCTGTCCTGGAAAAGGATGCTGCCGTGACGGTTGATTACCTTCT
CGGAAGCCCGTATGAAGCCATAAATCTTGTTTCGGGTTTAAACAAGATAAATTTTAGGT
CCATGACGGATGTGGTAGATTCCATACCATCGCTCTTAAATGAGCGTAAGGTGTGTGTC
TTCCAGAATGACGACAGTTCGTCGTTTTACATTCGGAAATGGGCCAACTTCCTTCAGGA
AGTTTCGGCAGTTTTACCGGTAGGAACCGGTAAATCCTCCACAATAGTTCTAACTTAG

Fig. 1

ATGTTTAGCAGAAGTTCCTCTACTCGCAGCTCCCTTGTGGGGAGCAGGAGTGGCTCCAT
TTTTGGAGGGGGATCTGTTAAGAAGTCTAGTACTGTGAGGGGGTTCTCTGCCGGTCTTG
AAAGATCGCGAGGATTACCTTCCGCCAGCGCTGGTGAAAACCAGATCTCGCTGCCGGGG
CTTAGGATCCCAGTTAAGGCTTCTTCACAACCGGGAAATTACTACCTTAAGGAGAGAGG
TATTGATTTGCCAATTGTGCAACAGCAGAAGTTTCTAGCCGCTGACGGCAAAGAAATGG
GGGAGTGTTACCTTTTGGACACTTCCCGAACTGATCTGTTGGACGCTGCCAAAGCAGCG
TTAAACGAGTCTAATCTTCTTGAATTCAACAAATTTAAGGAATTTAAGAAGTATAAGGG
AAAGAATAATGAATTCTCTTTGGTTGAGGCATCAGTTTTTGATAAACTGATCAGGAAGG
ACGATTCTCCCATACACCTTAACAGGCTTTTAATAGCTGTTTTACCTGCCGTAGGAAAA
GGAACACCAGGAACCGCACGAATTAAAATTCGTGACGCGCGCCTGGATGATGGTTATGG
TGAGCTTTTTAGTTCTGAAAATCGTGTGGACTCTGGCTACATTTATTGTATAAATGTAG
GTTATTCTGTTCCTAAGTCTGAAATCGATTACAAAATCAATATTGATTTTGCCGGGGTA
CCCATCAAAGATGGTAAGTCCCCGATTTGGGTCAAGGCTGCCTTCTCTTTAGCTGGTGG
CCCCCCTGTGTTCCTTGATGGAACAATGAGCTTGGGTGCTGAGATTTTGCCCGACTCTC
ATAAAGAGCTGTTGGGCACCTCTGCTTTGTTGTTGAATGAGGCGAATTCTAATAGGAAG
TCGTTCTCTGGTGATGACGGAGAGCTTAGAAGGGATTACCCTTATAAGCGTTTTGAGGA
AATTTCACCTTTGGATTCTATAAGTCAGGTCGATACGGCCAGTCAAGACTCCGTTAATG
AGGTGAACACCGAAAATGTTCAAAACGGTACTGGTGAGGTGTATTTGGCACCTCCTTCA
CATTCCGTTTATTAA

Fig. 2

| | | | | | | | | | | | | | | | |
|---|---|---|---|---|---|---|---|---|---|---|---|---|---|---|---|
| Met | Ala | Lys | Lys | Ala | Val | Pro | Pro | Ile | Val | Lys | Ala | Gln | Tyr | Glu | Leu |
| 1 | | | | 5 | | | | | 10 | | | | | 15 | |
| Tyr | Asn | Arg | Lys | Leu | Asn | Arg | Ala | Ile | Lys | Val | Ser | Gly | Ser | Gln | Lys |
| | | | 20 | | | | | 25 | | | | | 30 | | |
| Lys | Leu | Asp | Ala | Ser | Phe | Val | Gly | Phe | Ser | Glu | Ser | Ser | Asn | Pro | Glu |
| | | 35 | | | | | 40 | | | | | 45 | | | |
| Thr | Gly | Lys | Pro | His | Ala | Asp | Met | Ser | Met | Ser | Ala | Lys | Val | Lys | Arg |
| | 50 | | | | | 55 | | | | | 60 | | | | |
| Val | Asn | Thr | Trp | Leu | Lys | Asn | Phe | Asp | Arg | Glu | Tyr | Trp | Asp | Asn | Gln |
| 65 | | | | | 70 | | | | | 75 | | | | | 80 |
| Phe | Ala | Ser | Lys | Pro | Val | Pro | Arg | Pro | Ala | Lys | Gln | Ala | Leu | Lys | Gly |
| | | | | 85 | | | | | 90 | | | | | 95 | |
| Ser | Ser | Ser | Lys | Pro | Gln | Gln | Arg | Asp | Glu | Gly | Glu | Val | Val | Phe | Thr |
| | | | 100 | | | | | 105 | | | | | 110 | | |
| Arg | Lys | Asp | Ser | Gln | Lys | Ser | Val | Arg | Thr | Val | Ser | Tyr | Trp | Val | Cys |
| | | 115 | | | | | 120 | | | | | 125 | | | |
| Thr | Pro | Glu | Lys | Ser | Met | Lys | Pro | Leu | Lys | Tyr | Lys | Glu | Asp | Glu | Asn |
| | 130 | | | | | 135 | | | | | 140 | | | | |
| Val | Val | Glu | Val | Thr | Phe | Asn | Asp | Leu | Thr | Ala | Gln | Lys | Ala | Gly | Asp |
| 145 | | | | | 150 | | | | | 155 | | | | | 160 |
| Lys | Leu | Val | Ser | Ile | Leu | Leu | Glu | Ile | Asn | Val | Val | Gly | Gly | Ala | Val |
| | | | | 165 | | | | | 170 | | | | | 175 | |
| Asp | Asp | Lys | Gly | Arg | Val | Ala | Val | Leu | Glu | Lys | Asp | Ala | Ala | Val | Thr |
| | | | 180 | | | | | 185 | | | | | 190 | | |
| Val | Asp | Tyr | Leu | Leu | Gly | Ser | Pro | Tyr | Glu | Ala | Ile | Asn | Leu | Val | Ser |
| | | 195 | | | | | 200 | | | | | 205 | | | |
| Gly | Leu | Asn | Lys | Ile | Asn | Phe | Arg | Ser | Met | Thr | Asp | Val | Val | Asp | Ser |
| | 210 | | | | | 215 | | | | | 220 | | | | |
| Ile | Pro | Ser | Leu | Leu | Asn | Glu | Arg | Lys | Val | Cys | Val | Phe | Gln | Asn | Asp |
| 225 | | | | | 230 | | | | | 235 | | | | | 240 |
| Asp | Ser | Ser | Ser | Phe | Tyr | Ile | Arg | Lys | Trp | Ala | Asn | Phe | Leu | Gln | Glu |
| | | | | 245 | | | | | 250 | | | | | 255 | |
| Val | Ser | Ala | Val | Leu | Pro | Val | Gly | Thr | Gly | Lys | Ser | Ser | Thr | Ile | Val |
| | | | 260 | | | | | 265 | | | | | 270 | | |
| Leu | Thr | | | | | | | | | | | | | | |

Fig. 3

| | | | | | | | | | | | | | | | |
|---|---|---|---|---|---|---|---|---|---|---|---|---|---|---|---|
| Met | Phe | Ser | Arg | Ser | Ser | Ser | Thr | Arg | Ser | Ser | Leu | Val | Gly | Ser | Arg |
| 1 | | | | 5 | | | | | 10 | | | | | 15 | |
| Ser | Gly | Ser | Ile | Phe | Gly | Gly | Gly | Ser | Val | Lys | Lys | Ser | Ser | Thr | Val |
| | | | 20 | | | | | 25 | | | | | 30 | | |
| Arg | Gly | Phe | Ser | Ala | Gly | Leu | Glu | Arg | Ser | Arg | Gly | Leu | Pro | Ser | Ala |
| | | 35 | | | | | 40 | | | | | 45 | | | |
| Ser | Ala | Gly | Glu | Asn | Gln | Ile | Ser | Leu | Pro | Gly | Leu | Arg | Ile | Pro | Val |
| | 50 | | | | | 55 | | | | | 60 | | | | |
| Lys | Ala | Ser | Ser | Gln | Pro | Gly | Asn | Tyr | Tyr | Leu | Lys | Glu | Arg | Gly | Ile |
| 65 | | | | | 70 | | | | | 75 | | | | | 80 |
| Asp | Leu | Pro | Ile | Val | Gln | Gln | Gln | Lys | Phe | Leu | Ala | Ala | Asp | Gly | Lys |
| | | | | 85 | | | | | 90 | | | | | 95 | |
| Glu | Met | Gly | Glu | Cys | Tyr | Leu | Leu | Asp | Thr | Ser | Arg | Thr | Asp | Leu | Leu |
| | | | 100 | | | | | 105 | | | | | 110 | | |
| Asp | Ala | Ala | Lys | Ala | Ala | Leu | Asn | Glu | Ser | Asn | Leu | Leu | Glu | Phe | Asn |
| | | 115 | | | | | 120 | | | | | 125 | | | |
| Lys | Phe | Lys | Glu | Phe | Lys | Lys | Tyr | Lys | Gly | Lys | Asn | Asn | Glu | Phe | Ser |
| | 130 | | | | | 135 | | | | | 140 | | | | |
| Leu | Val | Glu | Ala | Ser | Val | Phe | Asp | Lys | Leu | Ile | Arg | Lys | Asp | Asp | Ser |
| 145 | | | | | 150 | | | | | 155 | | | | | 160 |
| Pro | Ile | His | Leu | Asn | Arg | Leu | Leu | Ile | Ala | Val | Leu | Pro | Ala | Val | Gly |
| | | | | 165 | | | | | 170 | | | | | 175 | |
| Lys | Gly | Thr | Pro | Gly | Thr | Ala | Arg | Ile | Lys | Ile | Arg | Asp | Ala | Arg | Leu |
| | | | 180 | | | | | 185 | | | | | 190 | | |
| Asp | Asp | Gly | Tyr | Gly | Glu | Leu | Phe | Ser | Ser | Glu | Asn | Arg | Val | Asp | Ser |
| | | 195 | | | | | 200 | | | | | 205 | | | |
| Gly | Tyr | Ile | Tyr | Cys | Ile | Asn | Val | Gly | Tyr | Ser | Val | Pro | Lys | Ser | Glu |
| | 210 | | | | | 215 | | | | | 220 | | | | |
| Ile | Asp | Tyr | Lys | Ile | Asn | Ile | Asp | Phe | Ala | Gly | Val | Pro | Ile | Lys | Asp |
| 225 | | | | | 230 | | | | | 235 | | | | | 240 |
| Gly | Lys | Ser | Pro | Ile | Trp | Val | Lys | Ala | Ala | Phe | Ser | Leu | Ala | Gly | Gly |
| | | | | 245 | | | | | 250 | | | | | 255 | |
| Pro | Pro | Val | Phe | Leu | Asp | Gly | Thr | Met | Ser | Leu | Gly | Ala | Glu | Ile | Leu |
| | | | 260 | | | | | 265 | | | | | 270 | | |
| Pro | Asp | Ser | His | Lys | Glu | Leu | Leu | Gly | Thr | Ser | Ala | Leu | Leu | Leu | Asn |
| | | 275 | | | | | 280 | | | | | 285 | | | |
| Glu | Ala | Asn | Ser | Asn | Arg | Lys | Ser | Phe | Ser | Gly | Asp | Asp | Gly | Glu | Leu |
| | 290 | | | | | 295 | | | | | 300 | | | | |
| Arg | Arg | Asp | Tyr | Pro | Tyr | Lys | Arg | Phe | Glu | Glu | Ile | Ser | Pro | Leu | Asp |
| 305 | | | | | 310 | | | | | 315 | | | | | 320 |
| Ser | Ile | Ser | Gln | Val | Asp | Thr | Ala | Ser | Gln | Asp | Ser | Val | Asn | Glu | Val |
| | | | | 325 | | | | | 330 | | | | | 335 | |
| Asn | Thr | Glu | Asn | Val | Gln | Asn | Gly | Thr | Gly | Glu | Val | Tyr | Leu | Ala | Pro |
| | | | 340 | | | | | 345 | | | | | 350 | | |
| Pro | Ser | His | Ser | Val | Tyr | | | | | | | | | | |
| | | 355 | | | | | | | | | | | | | |

Fig. 4

AGGTTTTAAAGAAGTTAATCTACTCGCAGCTCCCTTGTGGGGAGCAGGAGTGGCTCCATTTTTGGAGGGGGATCTG
TTAAGAAGTCTAGTACTGTGAGGGGGTTCTCTGCCGGTCTTGAAAGATCGCGAGGATTACCTTCCGCCAGCGCTGG
TGAAAACCAGATCTCGCTGCCGGGGCTTAGGATCCCAGTTAAGGCTTCTTCACAACCGGGAAATTACTACCTTAAG
GAGAGAGGTATTGATTTGCCAATTGTGCAACAGCAGAAGTTTCTAGCCGCTGACGGCAAAGAAATGGGGGAGTGTT
ACCTTTTGGACACTTCCCGAACTGATCTGTTGGACGCTGCCAAAGCAGCGTTAAACGAGTCTAATCTTCTTGAATT
CAACAAATTTAAGGAATTTAAGAAGTATAAGGGAAAGAATAATGAATTCTCTTTGGTTGAGGCATCAGTTTTTGAT
AAACTGATCAGGAAGGACGATTCTCCCATACACCTTAACAGGCTTTTAATAGCTGTTTTACCTGCCGTAGGAAAAG
GAACACCAGGAACCGCACGAATTAAAATTCGTGACGCGCGCCTGGATGATGGTTATGGTGAGCTTTTTAGTTCTGA
AAATCGTGTGGACTCTGGCTACATTTATTGTATAAATGTAGGTTATTCTGTTCCTAAGTCTGAAATCGATTACAAA
ATCAATATTGATTTTGCCGGGGTACCCATCAAAGATGGTAAGTCCCCGATTTGGGTCAAGGCTGCCTTCTCTTTAG
CTGGTGGCCCCCCTGTGTTCCTTGATGGAACAATGAGCTTGGGTGCTGAGATTTTGCCCGACTCTCATAAAGAGCT
GTTGGGCACCTCTGCTTTGTTGTTGAATGAGGCGAATTCTAATAGGAAGTCGTTCTCTGGTGATGACGGAGAGCTT
AGAAGGGATTACCCTTATAAGCGTTTTGAGGAAATTTCACCTTTGGATTCTATAAGTCAGGTCGATACGGCCAGTC
AAGACTCCGTTAATGAGGTGAACACCGAAAATGTTCAAAACGGTACTGGTGAGGTGTATTTGGCACCTCCTTCACA
TTCCGTTTATTAA

Fig. 5A

ATGTCTACTCGCAGCTCCCTTGTGGGGAGCAGGAGTGGCTCCATTTTTGGAGGGGGATCTGTTAAGAAGTCTAGTA
CTGTGAGGGGGTTCTCTGCCGGTCTTGAAAGATCGCGAGGATTACCTTCCGCCAGCGCTGGTGAAAACCAGATCTC
GCTGCCGGGGCTTAGGATCCCAGTTAAGGCTTCTTCACAACCGGGAAATTACTACCTTAAGGAGAGAGGTATTGAT
TTGCCAATTGTGCAACAGCAGAAGTTTCTAGCCGCTGACGGCAAAGAAATGGGGGAGTGTTACCTTTTGGACACTT
CCCGAACTGATCTGTTGGACGCTGCCAAAGCAGCGTTAAACGAGTCTAATCTTCTTGAATTCAACAAATTTAAGGA
ATTTAAGAAGTATAAGGGAAAGAATAATGAATTCTCTTTGGTTGAGGCATCAGTTTTTGATAAACTGATCAGGAAG
GACGATTCTCCCATACACCTTAACAGGCTTTTAATAGCTGTTTTACCTGCCGTAGGAAAAGGAACACCAGGAACCG
CACGAATTAAAATTCGTGACGCGCGCCTGGATGATGGTTATGGTGAGCTTTTTAGTTCTGAAAATCGTGTGGACTC
TGGCTACATTTATTGTATAAATGTAGGTTATTCTGTTCCTAAGTCTGAAATCGATTACAAAATCAATATTGATTTT
GCCGGGGTACCCATCAAAGATGGTAAGTCCCCGATTTGGGTCAAGGCTGCCTTCTCTTTAGCTGGTGGCCCCCCTG
TGTTCCTTGATGGAACAATGAGCTTGGGTGCTGAGATTTTGCCCGACTCTCATAAAGAGCTGTTGGGCACCTCTGC
TTTGTTGTTGAATGAGGCGAATTCTAATAGGAAGTCGTTCTCTGGTGATGACGGAGAGCTTAGAAGGGATTACCCT
TATAAGCGTTTTGAGGAAATTTCACCTTTGGATTCTATAAGTCAGGTCGATACGGCCAGTCAAGACTCCGTTAATG
AGGTGAACACCGAAAATGTTCAAAACGGTACTGGTGAGGTGTATTTGGCACCTCCTTCACATTCCGTTTATTAA

Fig. 5B

ATGTTTAGCAGAAGCAGGAGTGGCTCCATTTTTGGAGGGGGATCTGTTAAGAAGTCTAGTACTGTGAGGGGGTTCT
CTGCCGGTCTTGAAAGATCGCGAGGATTACCTTCCGCCAGCGCTGGTGAAAACCAGATCTCGCTGCCGGGGCTTAG
GATCCCAGTTAAGGCTTCTTCACAACCGGGAAATTACTACCTTAAGGAGAGAGGTATTGATTTGCCAATTGTGCAA
CAGCAGAAGTTTCTAGCCGCTGACGGCAAAGAAATGGGGGAGTGTTACCTTTTGGACACTTCCCGAACTGATCTGT
TGGACGCTGCCAAAGCAGCGTTAAACGAGTCTAATCTTCTTGAATTCAACAAATTTAAGGAATTTAAGAAGTATAA
GGGAAAGAATAATGAATTCTCTTTGGTTGAGGCATCAGTTTTTGATAAACTGATCAGGAAGGACGATTCTCCCATA
CACCTTAACAGGCTTTTAATAGCTGTTTTACCTGCCGTAGGAAAAGGAACACCAGGAACCGCACGAATTAAAATTC
GTGACGCGCGCCTGGATGATGGTTATGGTGAGCTTTTTAGTTCTGAAAATCGTGTGGACTCTGGCTACATTTATTG
TATAAATGTAGGTTATTCTGTTCCTAAGTCTGAAATCGATTACAAAATCAATATTGATTTTGCCGGGGTACCCATC
AAAGATGGTAAGTCCCCGATTTGGGTCAAGGCTGCCTTCTCTTTAGCTGGTGGCCCCCCTGTGTTCCTTGATGGAA
CAATGAGCTTGGGTGCTGAGATTTTGCCCGACTCTCATAAAGAGCTGTTGGGCACCTCTGCTTTGTTGTTGAATGA
GGCGAATTCTAATAGGAAGTCGTTCTCTGGTGATGACGGAGAGCTTAGAAGGGATTACCCTTATAAGCGTTTTGAG
GAAATTTCACCTTTGGATTCTATAAGTCAGGTCGATACGGCCAGTCAAGACTCCGTTAATGAGGTGAACACCGAAA
ATGTTCAAAACGGTACTGGTGAGGTGTATTTGGCACCTCCTTCACATTCCGTTTATTAA

Fig. 5C

ATGTTTAGCAGAAGTTCCTCTACTCGCAGCTCCCTTGTGGGGAGCAGGAGTGGCTCCATTTTTGGAGGGGGATCTG
TTAAGAAGTCTAGTACTGTGAGGGGGTTCTCTCGAGGATTACCTTCCGCCAGCGCTGGTGAAAACCAGATCTCGCT
GCCGGGGCTTAGGATCCCAGTTAAGGCTTCTTCACAACCGGGAAATTACTACCTTAAGGAGAGAGGTATTGATTTG
CCAATTGTGCAACAGCAGAAGTTTCTAGCCGCTGACGGCAAAGAAATGGGGGAGTGTTACCTTTTGGACACTTCCC
GAACTGATCTGTTGGACGCTGCCAAAGCAGCGTTAAACGAGTCTAATCTTCTTGAATTCAACAAATTTAAGGAATT
TAAGAAGTATAAGGGAAAGAATAATGAATTCTCTTTGGTTGAGGCATCAGTTTTTGATAAACTGATCAGGAAGGAC
GATTCTCCCATACACCTTAACAGGCTTTTAATAGCTGTTTTACCTGCCGTAGGAAAAGGAACACCAGGAACCGCAC
GAATTAAAATTCGTGACGCGCGCCTGGATGATGGTTATGGTGAGCTTTTTAGTTCTGAAAATCGTGTGGACTCTGG
CTACATTTATTGTATAAATGTAGGTTATTCTGTTCCTAAGTCTGAAATCGATTACAAAATCAATATTGATTTTGCC
GGGGTACCCATCAAAGATGGTAAGTCCCCGATTTGGGTCAAGGCTGCCTTCTCTTTAGCTGGTGGCCCCCCTGTGT
TCCTTGATGGAACAATGAGCTTGGGTGCTGAGATTTTGCCCGACTCTCATAAAGAGCTGTTGGGCACCTCTGCTTT
GTTGTTGAATGAGGCGAATTCTAATAGGAAGTCGTTCTCTGGTGATGACGGAGAGCTTAGAAGGGATTACCCTTAT
AAGCGTTTTGAGGAAATTTCACCTTTGGATTCTATAAGTCAGGTCGATACGGCCAGTCAAGACTCCGTTAATGAGG
TGAACACCGAAAATGTTCAAAACGGTACTGGTGAGGTGTATTTGGCACCTCCTTCACATTCCGTTTATTAA

Fig. 5D

DEVELOPMENT OF RESISTANCE TO RASPBERRY BUSHY DWARF VIRUS

This application is a continuation-in-part of U.S. application Ser. No. 09/737,719, filed on Dec. 15, 2000 (pending), which claims priority to U.S. Provisional application Ser. No. 60/171,018 filed on Dec. 15, 1999, both of which are expressly incorporated herein by reference in their entirety.

This work is supported in part by the U.S. Department of Agriculture under Cooperative Research and Development Agreement No. 58-3K95-M-495. Accordingly, the U.S. Government has certain rights in this invention.

FIELD OF THE INVENTION

The present invention relates to modified raspberry bushy dwarf virus (RBDV) proteins and the nucleic acid sequences which encode them. The invention also relates to RBDV resistant transgenic plants comprising nucleic acid sequences which encode modified RBDV proteins and methods of inducing resistance to RBDV in raspberry plants by transforming them with plant expression vectors comprising such nucleic acid sequences.

References

Abel P. P. et al. Science. 232(4751):738–43, 1986.
Adams D. O. and Yang S. F., Plant Physiology 70:117–123, 1977.
Altschul et al., Nucl. Acids Res. 25(17) 3389–3402, 1997.
Ausubel F. M. et al., Eds., CURRENT PROTOCOLS IN MOLECULAR BIOLOGY, John Wiley & Sons, Inc., Copyright (c)1987, 1988, 1989, 1990, 1993 by Current Protocols Anderson W. C., Acta Hort 112:13–20. 1980.
Barbara D. J., Jones, A. T., Henderson S. J., Wilson S. C. and Knight V. H., Annals of Applied Biology 105:49–53, 1984.
Beachy et al., Ann. Rev. Phytopathol. 28:451, 1990.
Becker D., Kemper E., Schell J. and Masterson R., Plant Mol Biol 20:1195–1197, 1992.
Chang S. et al., *Plant Molecular Biology Reporter,* 11(2):113–116, 1993.
Cooper B. et al., *Virology.* 206:3-7-313, 1995.
Crossway, Mol. *Gen. Genet,* 202:179–185, 1985.
Daubney H. A., Freeman, J. A. and R. Stace-Smith, Hortscience 17:645–657, 1982.
Doyle J. J. and Doyle J. L., *Focus* 12:13–15, 1990.
Fitchen, J. H. and Beachy R. N., *Ann. Rev. Microbiol.* 47:739–763, 1993.
Fraley et al., *Proc Natl Acad Sci USA* 79:1859–1863, 1982.
Fraley et al., Proc Natl Acad Sci USA 80:4803, 1983.
From et al., Proc. Nat Acad Sci USA 82:5824 1985.
Garfinkel D. J. and Nester E. W., *J Bacteriol.* 144:732–743, 1980.
Gelvin S. B., Schilperoort R. A., Varma D. P. S., eds. Plant Molecular Biology Manual, 1990.
Harlow and Lane, ANTIBODIES, A LABORATORY MANUAL, Cold Spring Harbor, 1988.
Hood E. E. et al., Transgenic Res. 2:208–218, 1993.
Horsch et al., *Science* 233:496–498, 1984.
Hu et al., J. Phyopathol. 128:1–14, 1990.
Hooykaas P. J., and Schilperoot R. A., in TRENDS IN BIOCHEMICAL SCIENCES, International Union of Biochemistry and Elsevier Science Publishers, v. 10(8):307–309, 1985.
Klein et al., *Nature* 327:70–73, 1987.
Kokko H. I. et al., Biotechniques 20(5):842–6, 1996.
Krens et al., *Nature* 296:72–74, 1982.
Knudsen and Muller, *Planta* 185:330–336, 1991.
Kunkel T. A., Roberts J. D. and Zakour R., *Methods Enzymol.* 154:367–382, 1987.
Lincoln J. E. and Fischer R. L., Mol. Gen. Genet. 212:71–75, 1988.
MacDonald S. G. et al., Phytopathol. 81:210–214, 1991.
MacKenzie D. J. et al., Plant Disease 81:222–226, 1996.
Maniatis et al., MOLECULAR CLONING: A LABORATORY MANUAL, 2nd Edition, 1989.
Martin R. R. et al., *Acta Hortic.* 471:72–76, 1998.
Mathews H. et al., *Plant Cell Reports* 14:471–476, 1995.
Mathews H. et al., *Transgenic Res.* 7:123–131, 1998.
Murashige T., Skoog F., *Physiol. Plant* 15:473–497, 1962.
Nagel R. et al., *FEMS Microbiol. Lett* 67:325, 1990.
Natsuaki T. et al., *J Gen Virol* 72:2183–2189, 1991.
Sambrook J. et al., MOLECULAR CLONING: A LABORATORY MANUAL, Cold Spring Harbor Laboratory Press, Cold Spring Harbor, NY, Vol. 2 Chapters 9 and 11, 1989.
Schell J., *Science* 237:1176–1183, 1987.
Verdaguer et al., *Plant Molecular Biology* 37:1055–1067, 1998.
Ziegler A. et al., *J Gen Virol* 73 (Pt 12): 3213–3218, 1992.

BACKGROUND OF THE INVENTION

Raspberry production in a number of geographic locations, including the Pacific Northwest, Oregon and Washington in the USA and southwestern British Columbia in Canada, has increased dramatically during the past decade. The increase in production has been the result of a move to more mechanical harvesting of raspberries resulting in reduced labor costs, a change in cultivars and an increase in acreage. Prior to 1980, the cultivar, Willamette was the most widely planted raspberry cultivar in this region. Since the early 1980's, the cultivar Meeker has become the cultivar of choice for most growers because of yield, resistance to root rot and the high quality of the berries for the valuable whole frozen and fresh berry markets. Hence, cultivar Meeker has become a suitable replacement for cultfivar Willamette as a processing berry.

The change in cultivars has resulted in the potential for an increased incidence of raspberry bushy dwarf virus (RBDV) since the cultivar Willamette is immune to the type strain of the virus while the cultivar Meeker is susceptible (Daubeny et al., 1982). In 1995, growers in Whatcom Co. (Fraser Valley in Washington) observed increased crumbly fruit in cultivar Meeker plantings, and initial tests showed these plantings had a high incidence of RBDV infection. Such crumbly fruit is not useful for the whole frozen or fresh berry markets. Surveys conducted during 1996–1998 showed that RBDV occurred in most raspberry fields of susceptible cultivars by the second fruiting season in the Fraser Valley (northwest Washington and southwest British Columbia). Also, the infection rate in these fields approached 100% by the fifth cropping season (Martin, 1998).

It is therefore of interest to develop a means to manage RBDV infection in raspberry (*Rubus idaeus*) cultivars such as Meeker that are susceptible to the virus.

SUMMARY OF THE INVENTION

The invention provides RBDV coat and movement protein or polypeptide nucleic acid and amino acid sequences and modified or mutant forms thereof for use in the development of RBDV resistant transgenic plants.

In one aspect, the invention provides an isolated raspberry bushy dwarf virus (RBDV) protein or polypeptide selected from the group consisting of:

(a) a RBDV coat protein or polypeptide with an amino acid sequence having at least 80%, 90% or 95% sequence identity to the sequence presented as SEQ ID NO:2;

(b) a RBDV coat protein or polypeptide with the amino acid sequence presented as SEQ ID NO:2.

(c) a RBDV movement protein or polypeptide with an amino acid sequence having at least 80%, 90% or 95% sequence identity to the sequence presented as SEQ ID NO:4; and (d) a RBDV movement protein or polypeptide with the amino acid sequence presented as SEQ ID NO:4.

In a related aspect, the invention provides an isolated RBDV polynucleotide selected from the group consisting of:

(a) a polynucleotide with a nucleic acid sequence which encodes or is complementary to a sequence which encodes a RBDV coat protein or polypeptide having at least 80%, 90% or 95% sequence identity to the sequence presented as SEQ ID NO:2;

(b) a polynucleotide with a nucleic acid sequence which encodes or is complementary to a sequence which encodes the RBDV coat protein or polypeptide having the sequence presented as SEQ ID NO:2;

(c) a polynucleotide sequence with the nucleic acid sequence presented as SEQ ID NO:1, which encodes or is complementary to a sequence which encodes a RBDV coat protein or polypeptide;

(d) a polynucleotide with a nucleic acid sequence that hybridizes, under high stringency conditions to the RBDV coat protein-encoding nucleic acid sequence presented as SEQ ID NO:1, or the complement or a fragment thereof;

(e) a polynucleotide comprising a nucleic acid sequence which encodes or is complementary to a sequence which encodes a RBDV movement protein or polypeptide having at least 80%, 90% or 95% sequence identity to the sequence presented as SEQ ID NO:4;

(f) a polynucleotide comprising the nucleic acid sequence which encodes or is complementary to a sequence which encodes a RBDV movement protein or polypeptide having the sequence presented as SEQ ID NO:4;

(g) a polynucleotide sequence with the nucleic acid sequence presented as SEQ ID NO:3, which encodes or is complementary to a sequence which encodes a RBDV movement protein or polypeptide; and (h) a polynucleotide with a nucleic acid sequence that hybridizes, under high stringency conditions to the RBDV movement protein-encoding nucleic acid sequence presented as SEQ ID NO:3, or the complement or a fragment thereof.

In another aspect, the invention provides an isolated polynucleotide which encodes a raspberry bushy dwarf virus (RBDV) coat or movement protein or polypeptide, wherein expression of the polynucleotide in a transgenic plant is associated with enhanced resistance to infection by RBDV.

The polynucleotide may encode a wild type, mutated or modified RBDV coat or movement protein or polypeptide. Plant transformation vectors, transgenic plant cells and transgenic plants comprising such RBDV coat or movement protein or polypeptide-encoding polynucelotides are within the scope of the invention.

In a further aspect, the invention provides transgenic plants that exhibit enhanced resistance to infection by RBDV and methods for producing the same.

These and other objects and features of the invention will become more fully apparent when the following detailed description of the invention is read in conjunction with the accompanying drawings.

BRIEF DESCRIPTION OF THE FIGURES

FIG. 1 depicts the nucleotide sequence which encodes the coat protein of a Pacific Northwest isolate of Raspberry Bushy Dwarf Virus (RBDV; SEQ ID NO:1).

FIG. 2 depicts the nucleotide sequence which encodes the movement protein of a Pacific Northwest isolate of RBDV (SEQ ID NO:3).

FIG. 3 depicts the predicted amino acid sequence for the coat protein of a Pacific Northwest isolate of RBDV (SEQ ID NO:2), based on the nucleic acid sequence presented as SEQ ID NO:1.

FIG. 4 depicts the predicted amino acid sequence for the movement protein a Pacific Northwest isolate of RBDV (SEQ ID NO:4), based on the nucleic acid sequence presented as SEQ ID NO:2.

FIGS. 5A–D depict modified or mutant RBDV movement protein sequences (SEQ ID NO:13–SEQ ID NO:16).

DETAILED DESCRIPTION OF THE INVENTION

I. Definitions

Figure 6:
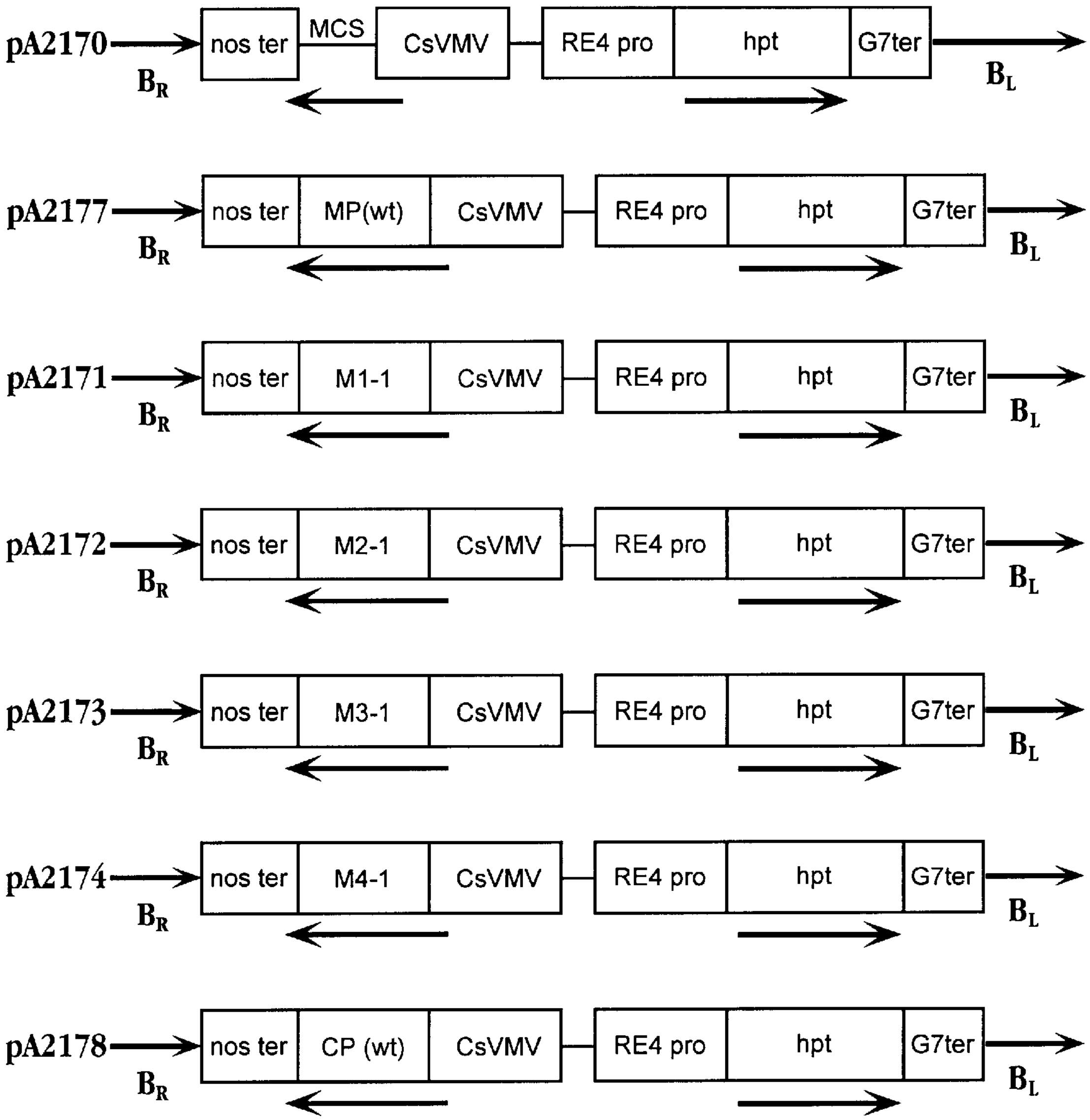
FIG. 6 is a schematic illustration of the binary vectors used to make the transgenic raspberry plants exemplified herein, identified as plasmids pAG-2170, pAG-2177, pAG-2171, pAG-2172, pAG-2173, pAG-2174 and pAG-2178. Arrows indicate the direction of T-DNA displacement or gene transcription. "Nos-ter" refers to nopaline synthase terminator; "MCS" refers to multiple cloning site; "CsVMV" refers to Cassava Vein Mottled Virus promoter; "RE4-pro" refers to raspberry E4 promoter; "hpt" refers to hygromycin phosphotransferase; "G7-ter" refers to gene 7 terminator; "$B_R$" refers to right border; "$B_L$" refers to left border; "MP(wt)" refers to the wild type movement protein coding sequence; "M1-1" refers to mutant movement protein 1 coding sequence; "M2-1" refers to mutant movement protein 2 coding sequence; "M3-1" refers to mutant movement protein 3 coding sequence; "M4-1" refers to mutant movement protein 4 coding sequence; and "CP(wt)" refers to wild type coat protein coding sequence.

As used herein, the term "Raspberry Bushy Dwarf Virus" or "RBDV" refers to a group of virus strains that individually or in combination infect raspberry (*Rubus idaeus*), resulting in damage to the fruit.

Amino acid residues are referred to herein by their standard single letter notations: A, alanine; C, cysteine; D, aspartic acid; E, glutamic acid; F, phenylalanine; G, glycine; H, histidine; I, isoleucine; K, lysine; L, leucine; M, methionine; N, asparagine; P, proline; Q, glutamine; R, arginine; S, serine; T, threonine; V, valine; W, tryptophan; Y, tyrosine.

The term "polypeptide" as used herein refers to a compound made up of a single chain of amino acid residues linked by peptide bonds. The term "protein" as used herein may be synonymous with the term "polypeptide" or may refer, in addition, to a complex of two or more polypeptides. In the context of the present invention, a "protein complex" refers to multiple copies of the same protein or protein fragment that bind to a single ribonucleotide fragment. Generally, but not always, polypeptides and proteins are formed predominantly of naturally occurring amino acids.

The terms "substantially purified" and "isolated", refer to molecules, either polypeptides or polynucleotides, that are removed from the components that naturally accompany them. Such polypeptides or polynucleotides have been separated from other components, and are typically at least 75% free, preferably 85% to 95% free and more preferably 98% or more free from other components with which they are naturally associated.

Variant polynucleotides may also encode variant amino acid sequences which contain amino acid insertions or deletions, or both. Furthermore, a variant polynucleotide may encode the same polypeptide as the reference polynucleotide sequence but, due to the degeneracy of the genetic code, has a polynucleotide sequence which is altered by one or more bases from the reference polynucleotide sequence.

As used herein, the term "polynucleotide" refers to a polymeric molecule having a backbone that supports bases capable of hydrogen bonding to typical polynucleotides, where the polymer backbone presents the bases in a manner to permit such hydrogen bonding in a sequence specific fashion between the polymeric molecule and a typical polynucleotide (e.g., single-stranded DNA). Such bases are typically inosine, adenosine, guanosine, cytosine, uracil and thymidine. Polymeric molecules include double and single stranded ribonucleic acids (RNA) and deoxyribonucleic acids (DNA), and may include polymers having backbone modifications such methylphosphonate linkages.

A nucleic acid may be double stranded, single stranded, or contain portions of both double stranded and single stranded sequence. The depiction of a single strand also defines the sequence of the other strand and thus also includes the complement of the sequence which is depicted.

As used herein, the term "recombinant nucleic acid" refers to a nucleic acid, originally formed in vitro, in general, by the manipulation of nucleic acid by endonucleases, in a form not normally found in nature.

As used herein, the terms "promoter" or "promoter segment" refer to a sequence of DNA that functions to direct transcription of a downstream gene. The promoter will generally be appropriate to the host cell in which the target gene is being expressed. The promoter together with other transcriptional and translational regulatory nucleic acid sequences (also termed "control sequences") are necessary to express a given gene. In general, the transcriptional and translational regulatory sequences include, but are not limited to, promoter sequences, ribosomal binding sites, transcriptional start and stop sequences, translational start and stop sequences, and enhancer or activator sequences.

As used herein, the term "regulatable promoter" refers to any promoter whose activity is affected by specific environmental or developmental conditions (e.g., a tomato E4 or E8 promoter).

As used herein, the term "constitutive promoter" refers to any promoter that directs RNA production in many or all tissues of a plant transformant at most times.

As used herein, the term "operably linked" relative to a recombinant DNA construct or vector means nucleotide components of the recombinant DNA construct or vector are in a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame.

As used herein, the term "gene" means the segment of RNA, DNA or copy DNA (cDNA) involved in producing a polypeptide chain, which may or may not include regions preceding and following the coding region, e.g. 5' untranslated (5' UTR) or "leader" sequences and 3' UTR or "trailer" sequences.

As used herein, the term "sequence identity" means nucleic acid or amino acid sequence identity in two or more aligned sequences, aligned using a sequence alignment program. Sequence searches are preferably carried out using a BLASTN or BLASTP program when evaluating a given nucleic acid or amino acid sequence, respectively, relative to sequences in public databases.

The BLASTX program is preferred for searching nucleic acid sequences that have been translated in all reading frames against amino acid sequences in the GenBank Protein Sequences and other public databases. The BLASTN program is preferred for searching nucleic acid sequences against a nucleic acid sequence database. Both BLASTN and BLASTX utilize the BLOSUM-62 matrix and are run using default parameters with an open gap penalty of 11.0, and an extended gap penalty of 1.0. [See, Altschul et al., 1997.]

The term % identity" herein and refers to the level of identity between two amino acid or nucleic acid sequences, as determined by a defined algorithm, and accordingly a homologue of a given sequence has at least about 70% or 80%, preferably about 90, 95 or 98% sequence identity over a length of the given sequence. It will be understood that the term "70% homology" means the same thing as 70% sequence identity.

A preferred alignment of selected sequences in order to determine "% identity" between two or more sequences, is performed using the CLUSTAL-W program in the Megaline DNASTAR program, operated with default parameters, including an open gap penalty/gap length penalty of 10.0. In some cases, the Clustal program from the Baylor Medical School: found at dot. imgen.bcm.tmc.edu:9331/multi-align/multi-align.html is used (with default parameters).

A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature (Tm) of the nucleic acid binding complex or probe. For example, "maximum stringency" typically occurs at about Tm-5° C. (5° below the Tm of the probe); "high stringency" at about 5–10° below the Tm; "intermediate stringency" at about 10–20° below the Tm of the probe; and "low stringency" at about 20–25° below the Tm. Functionally, maximum stringency conditions may be used to identify sequences having strict identity or near-strict identity with the hybridization probe, while high stringency conditions are used to identify sequences having about 80% or more sequence identity with the probe.

High stringency hybridization conditions are well known in the art (see, for example, Sambrook et al. (1989) Chapters 9 and 11, and in Ausubel et al., 1993, expressly incorporated by reference herein). An example of high stringency conditions includes hybridization at about 42° C. in 50% formamide, 5× SSC, 5× Denhardt's solution, 0.5% SDS and 100 $\mu$g/ml denatured carrier DNA followed by washing two times in 2× SSC and 0.5% SDS at room temperature and two additional times in 0.1× SSC and 0.5% SDS at 43° C.

A "heterologous" nucleic acid construct or sequence has a portion of the sequence which has been introduced into the plant cell in which it is expressed. Heterologous, with respect to a coding sequence may refer to a coding sequence that has been modified from the form in which it is found in nature. Generally, heterologous nucleic acid is introduced into a cell, by transfection, microinjection, electroporation, or the like. The sequences may contain a control sequence/DNA coding sequence combination that is the same as, or different from a control sequence/DNA coding sequence combination found in the native plant.

As used herein, the terms "chimeric nucleic acid construct" and "chimeric gene construct" are used interchangeably and refer to recombinant nucleic acid sequences which comprise a DNA coding sequence and control sequences required for expression of the coding sequence in a plant cell.

As used herein, the terms "transformed", "stably transformed" or "transgenic" with reference to a plant cell means the plant cell has a non-native (heterologous) nucleic acid sequence integrated into its genome which is maintained through two or more generations.

As used herein, the term "expression" refers to the process by which a polypeptide is produced based on the nucleic acid sequence of a gene. The process includes both transcription and translation.

The term "introduced" in the context of inserting a nucleic acid sequence into a cell, means "transfection", or "transformation" or "transduction" and includes reference to the incorporation of a nucleic acid sequence into a eukaryotic or prokaryotic cell. The nucleic acid sequence may be incorporated into the genome of the cell (for example, chromosome, plasmid, plastid, or mitochondrial DNA), converted into an autonomous replicon, or transiently expressed (for example, transfected mRNA).

As used herein the terms "raspberry bushy dwarf virus (RBDV) coat protein sequence" and "raspberry bushy dwarf virus (RBDV) coat protein polypeptide sequence" are used interchangeably and refer to a sequence that has at least 80% or 85% and preferably at least 90%, 95% or 98% sequence identity to the sequence presented as SEQ ID NO:2, or a fragment thereof which maintains the biological function of a wild type RBDV coat protein, and/or an isolated RBDV coat protein or polypeptide having the amino sequence presented as SEQ ID NO:2.

As used herein the terms "polynucleotide sequence which encodes a raspberry bushy dwarf virus (RBDV) coat protein" and "polynucleotide sequence which encodes a raspberry bushy dwarf virus (RBDV) coat polypeptide" refer to a polynucleotide sequence which encodes a sequence that has at least 80% or 85% and preferably at least 90%, 95% or 98% sequence identity to the sequence presented as SEQ ID NO:2, or a fragment thereof which maintains the biological function of a wild type RBDV coat protein, and/or an isolated polynucleotide sequence which encodes a RBDV coat protein having the amino sequence presented as SEQ ID NO:2. An exemplary RBDV coat protein-encoding polynucleotide sequence is presented herein as SEQ ID NO:1.

As used herein the terms "raspberry bushy dwarf virus (RBDV) movement protein sequence" and "raspberry bushy dwarf virus (RBDV) movement polypeptide sequence" are used interchangeably and refer to a sequence that has at least 80% or 85% and preferably at least 90%, 95% or 98% sequence identity to the sequence presented as SEQ ID NO:4, or a fragment thereof which maintains the biological function of a wild type RBDV movement protein, and/or an isolated RBDV movement protein or polypeptide having the amino sequence presented as SEQ ID NO:4.

As used herein the terms "polynucleotide sequence which encodes a raspberry bushy dwarf virus (RBDV) movement protein" and "polynucleotide sequence which encodes a raspberry bushy dwarf virus (RBDV) movement polypeptide" refer to a polynucleotide sequence which encodes a sequence that has at least 80% or 85% and preferably at least 90%, 95% or 98% sequence identity to the sequence presented as SEQ ID NO:4, or a fragment thereof which maintains the biological function of a wild type RBDV movement protein, or an isolated polynucleotide sequence which encodes a RBDV movement protein having the amino sequence presented as SEQ ID NO:4. An exemplary RBDV movement protein-encoding polynucleotide sequence is presented herein as SEQ ID NO:3.

As used herein, the terms "mutant RBDV protein or polypeptide" and "modified RBDV protein or polypeptide", are used interchangeably and refer to a RBDV coat or movement protein or polypeptide or fragment thereof encoded by a polynucleotide which has been modified relative to the polynucleotide which encodes a wild type RBDV protein or polypeptide, e.g., a wild type RBDV movement protein. In this aspect, the invention provides "mutant" or "modified" forms of the RBDV coat and movement protein-encoding nucleic acid sequences presented herein as SEQ ID NO:1 and SEQ ID NO:3, where the "mutant" or "modified" form lacks the biological activity of the wild type sequences presented herein. Exemplary modifications include insertions, deletions, substitutions, alteration of the start codons, insertion of one or more stop codons in the coding sequence, etc. Specific examples are presented herein as SEQ ID NO:13, SEQ ID NO:14, SEQ ID NO:15 and SEQ ID NO:16.

The exact sequence of "mutant" or "modified" RBDV coat or movement protein or polypeptide-encoding nucleic acid sequences can readily be determined by mutation or modification of the sequences presented herein as SEQ ID NO:1 or SEQ ID NO:3, followed by use of such modified forms to develop transgenic plants followed by testing of the plants for resistance to infection with RBDV, as further detailed below.

As used herein, the terms "RBDV-resistant plant" and "RBDV-resistant plant cell" refer to a transformed raspberry plant or plant cell, respectively, wherein the raspberry plant or plant cell is "resistant" to infection by RBDV. In other words, the raspberry plant or plant cell is either, not injectable with RBDV, or is less infectable than a non-transformed raspberry plant or plant cell. In general, this means the quality of fruit produced by the transformed raspberry plant or plant cell is more useful for the whole frozen or fresh berry markets than fruit derived from non-transformed raspberry plants or plant cells.

A "mutant", "modified" or "variant" polynucleotide sequence may encode a "mutant", "modified" or "variant" amino acid sequence which is altered by one or more amino acids from the reference (i.e., wild type) polypeptide sequence, or a nontranslatable RNA sequence. The mutant polynucleotide sequence generally includes at least one nucleic acid substitution, deletion or insertion, with nucleic acid substitutions preferred. The nucleic acid substitution, insertion or deletion may occur at any residue within a RBDV polypeptide or protein-encoding nucleic acid sequence.

As used herein, a "plant cell" refers to any cell derived from a plant, including undifferentiated tissue (e.g., callus) as well as plant seeds, pollen, progagules and embryos.

As used herein, the term "mature plant" refers to a fully differentiated plant.

As used herein, the terms "native" and "wild-type" relative to a plant trait, phenotype, plant cell or plant refers to the form in which that trait, phenotype, plant cell or plant is found in the same variety of plant in nature. Hence, a "native" or "wild-type" plant cell or plant is non-transgenic.

As used herein, the term "transgenic plant" refers to a plant that has incorporated a heterologous or exogenous nucleic acid sequence, i.e., a nucleic acid sequence which is not present in the native (non-transgenic or "untransformed") plant or plant cell. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic plant. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

II. Raspberry Bushy Dwarf Viruses (RBDV)

RBDV are a group of single-stranded RNA (ssRNA) positive-strand virus strains, which lack a DNA stage, that collectively or individually adversely effect fruiting and growth in raspberries. Infection with RBDV is of economic importance and limits the production of raspberries (Rubus species), blackberries (Bubus species), etc., throughout the world.

RBDV has been demonstrated to have a large component (designated RNA-1) which consists of 5449 nucleotides and contains one large open reading frame (ORF). The predicted polypeptide encoded by this ORF has been shown to have significant homology to ORFs of alfalfa mosaic virus (AIMV), brome mosaic virus (BMV), cucumber mosaic virus (CMV) and tobacco mosaic virus (TMV) (Ziegler et al., 1992).

Various strains of RBDV have been cloned and sequenced, with the sequence of the resistance-breaking strain (RBDV-RB) available in public databases. Exemplary sequences are provided at GenBank Accession Nos. S51557 (RNA-1), S55890 (RNA-2), and D01052 (RNA-3), respectively.

Alfalfa mosaic virus, which is in the monotypic genus alfamovirus and closely related to RBDV (ideaovirus), is known to have 3 genomic RNAs plus a subgenomic RNA, all of which have been sequenced. (See GenBank Accession Nos. M35389, M35975, M36391, for RNA-1, RNA-2 and RNA-3, respectively of the S-strain, and 100162, for RNA-4 of the L-strain.) Several ilarviruses (e.g., tobacco streak virus, prunus necrotic ringspot virus and apple mosaic virus), have also been completely or partially sequenced and the sequences are publicly available in GenBank.

The present invention provides the coding sequence for an RBDV D strain (or type) coat and movement protein (SEQ ID NO:1 and SEQ ID NO:3, respectively).

III. Wild Type RBDV Coat and Movement Protein Amino Acid and Nucleic Acid Sequences RBDV coat and movement protein coding sequences were obtained by performing the steps of (1) infecting *Chenopodium quinoa* plants with RBDV; (2) purifying virus from the infected plants; (3) isolating RNA from the purified virus; (4) carrying out a cDNA synthesis reaction; (5) performing PCR to obtain an RBDV fragment using oligonucleotide primers RBDVCP3' (SEQ ID NO:5) and RBDVCP5' (SEQ ID NO:6) for the coat protein, together with RBDVMP3' (SEQ ID NO:7) and RBDVMP5' (SEQ ID NO:8) for the movement protein, respectively; (6) ligating the fragments into cloning vectors; (7) sequencing a portion of the cloned sequences; and (8) using the product of the each sequencing reaction to design a different gene-specific primer for use in further sequencing until a full length cDNA sequence was obtained for the RBDV coat and movement proteins, respectively.

In cloning the RBDV sequences that serve as the basis for the present invention, RBDV was isolated from the *Rubus idaeus* clone OSU769, purified using the blueberry shock ilarvirus purification protocol described by MacDonald et al., 1991, followed by RNA extraction from the purified virus preparation of cDNA.

Exemplary RBDV protein or polypeptide amino acid sequences provided by the invention include, but are not limited to: (1) an isolated RBDV coat protein or polypeptide sequence, wherein the amino acid sequence of the coat protein or polypeptide has at least 80% or 85%, preferably at least 90%, 95% or 98% sequence identity to the sequence presented as SEQ ID NO:2, or a fragment thereof; (2) an isolated RBDV coat protein or polypeptide having the amino sequence presented as SEQ ID NO:2; (3) an isolated RBDV movement protein or polypeptide, wherein amino acid sequence of the movement protein or polypeptide has at least about 80% or 85%, preferably at least about 90%, 95% or 98% sequence identity to the sequence presented as SEQ ID NO:4 or a fragment thereof; or (4) an isolated RBDV movement protein or polypeptide having the amino sequence presented as SEQ ID NO:4.

Exemplary RBDV nucleic acid sequences of the invention include, but are not limited to: (1) an isolated RBDV coat protein or polypeptide-encoding nucleic acid sequence, wherein the amino acid sequence of the encoded coat protein or polypeptide has at least about 80% or 85%, preferably at least about 90%, 95% or 98% sequence identity to the sequence presented as SEQ ID NO:2 or a fragment thereof, (2) an isolated polynucleotide sequence which encodes a RBDV coat protein having the amino sequence presented as SEQ ID NO:2; (3) an isolated polynucleotide sequence that encodes a RBDV coat protein and has the nucleic acid sequence presented as SEQ ID NO:1, or a nucleic acid sequence which will hybridize to the sequence presented as SEQ ID NO:1 under high stringency conditions; (4) an isolated RBDV movement protein-encoding nucleic acid, wherein amino acid sequence of the movement protein or polypeptide has at least about 80% or 85%, preferably at least about 90%, 95% or 98% sequence identity to the sequence presented as SEQ ID NO:4, or a fragment thereof; (5) an isolated polynucleotide sequence which encodes a RBDV movement protein having the amino sequence presented as SEQ ID NO:4; and (6) an isolated polynucleotide sequence which encodes a RBDV movement protein and has the nucleic acid sequence presented as SEQ ID NO:3, or a nucleic acid sequence which will hybridize the sequence presented as SEQ ID NO:3 under high stringency conditions.

IV. Methods of Inducing Resistance to Raspberry Bushy Dwarf Virus (RBDV)

A. Methods of the Invention

The invention is directed to strategies for developing genetic resistance to RBDV in raspberry (*Rubus idaeus*)

cultivars that are susceptible to RBDV. The raspberry cultivar Meeker, which at present comprises about 70% of the production in the Pacific Northwest and is susceptible to RBDV infection was used to evaluate the effect of various modified RBDV proteins on resistance to the virus.

It has previously been shown that expression of a plant virus capsid or coat protein in a plant, can confer resistance to the homologous virus and to related viruses (Abel et al. 1986 and Beachy et al., 1990).

By way of example, a series of mutated RBDV movement protein-encoding nucleic acid sequences are presented herein, together with method for inducing resistance to RBDV by introducing such mutated RBDV movement protein-encoding nucleic acids into plants. It will be understood that the invention is related to modifications of the wild type RBDV coat protein and movement protein-encoding nucleic acid sequences provided herein and is not limited to the particular examples provided. In other words, the RBDV coat protein and movement protein-encoding nucleic acid sequences provided herein may be modified in any of a number of ways resulting in modified RBDV coat protein or movement protein-encoding nucleic acid sequences useful in the generation of RBDV-resistant raspberry plant cells and plants.

B. Modified Raspberry Bushy Dwarf Virus (RBDV) Polynucleotides, Polypeptides and Proteins As used herein, the terms "mutant RBDV protein or polypeptide" and "modified RBDV protein or polypeptide", are used interchangeably and refer to a RBDV coat or movement protein or polypeptide or fragment thereof encoded by a polynucleotide which has been modified relative to the polynucleotide which encodes a wild type RBDV protein or polypeptide, e.g., a wild type RBDV movement protein. In this aspect, the invention provides modified forms of the RBDV coat and movement protein-encoding nucleic acid sequences presented herein as SEQ ID NO:1 and SEQ ID NO:3, where the "mutant" or "modified" form lacks the biological activity of the wild type sequences presented herein. Exemplary modifications include insertions, deletions, substitutions, alteration of the start codons, insertion of one or more stop codons in the coding sequence, etc. Specific examples are presented herein as SEQ ID NO:13, SEQ ID NO:14, SEQ ID NO:15 and SEQ ID NO:16.

Such "mutant" or "modified" RBDV nucleic acid sequences are nucleic acid sequences which have typically been modified using chemical modification techniques which are well known in the art. In one exemplary approach a "mutant" or "modified" coding sequences for a RBDV coat or movement protein is generated using the Transformer site-directed mutagenesis kit (ClonTech). In general, the practice of the present invention employs, unless otherwise indicated, conventional techniques of molecular biology, microbiology, recombinant DNA, and immunology, which are within the skill of the art. Such techniques are explained fully in the literature. See, for example, "Molecular Cloning: A Laboratory Manual", Second Edition (Sambrook, Fritsch & Maniatis, 1989), "Animal Cell Culture" (R. I. Freshney, ed., 1987); "Current Protocols in Molecular Biology" (F. M. Ausubel et al, eds., 1987); and "Current Protocols in Immunology" (J. E. Coligan et al., eds., 1991), hereby expressly incorporated herein by reference.

The exact sequence of "mutant" or "modified" RBDV coat or movement protein or polypeptide-encoding nucleic acid sequences can readily be determined by mutation or modification of the sequences presented herein as SEQ ID NO:1 or SEQ ID NO:3, followed by testing of such truncated forms in transgenic plants for the ability to promote resistance to infection with RBDV, as further detailed below.

A "mutant", "modified" or "variant" polynucleotide sequence may encode a "mutant", "modified" or "variant" amino acid sequence which is altered by one or more amino acids from the reference (i.e., wild type) polypeptide sequence, or a nontranslatable RNA sequence. The mutant polynucleotide sequence generally includes at least one nucleic acid substitution, deletion or insertion, with nucleic acid substitutions preferred. The nucleic acid substitution, insertion or deletion may occur at any residue within a RBDV polypeptide or protein-encoding nucleic acid sequence.

C. Nucleic Acid Constructs

Standard Agrobacterium binary vectors are known to those of skill in the art and many are commercially available. Expression vectors typically include polyadenylation sites, translation regulatory sequences (e.g., translation start sites), introns and splice sites, enhancer sequences (which can be inducible, tissue specific or constitutive), and may further include 5' and 3' regulatory and flanking sequences.

An exemplary binary vector suitable for use in practicing the invention includes at least one T-DNA border sequence (left, right or both); restriction endonuclease sites for the addition of one or more heterologous nucleic acid coding sequences [adjacent flanking T-DNA border sequence(s)]; a heterologous nucleic acid coding sequence (i.e., the sequence encoding a protein or polypeptide of interest), operably linked to appropriate regulatory sequences and to the directional T-DNA border sequences; a selectable marker-encoding nucleotide sequence which is functional in plant cells, operably linked to a promoter effective to express the selectable marker encoding sequence; a termination element for the selectable marker-encoding nucleotide sequence; a heterologous Ti-plasmid promoter; a nucleic acid sequence which facilitates replication in a secondary host (e.g., an *E. coli* origin of replication) and a nucleic acid sequence for selection in the secondary host, i.e., *E. coli.*

In general, a selected nucleic acid sequence is inserted into an appropriate restriction endonuclease site or sites in the vector. Standard methods for cutting, ligating and *E. coli* transformation, known to those of skill in the art, are used in constructing vectors for use in the present invention. See, for example, Sambrook et al., 1989 and Ausubel et al., 1989, expressly incorporated by reference herein.

In choosing a promoter it may be desirable to use a tissue-specific or developmentally regulated promoter for regulated expression in certain tissues without affecting expression in other tissues. Numerous examples of such promoters are known in the art. Alternatively, differential screening techniques may be used to isolate promoters expressed at specific (developmental) times, such as during fruit development. Constitutive promoters are preferred in practicing the methods of the invention.

Generally, methods for the construction of vectors for use in practicing the present invention are known to those of skill in the art. (See e.g., Maniatis et al., 1989; Ausubel et al., (c)1987, 1988, 1989, 1990, 1993; and Gelvin et al., 1990), all three of which are expressly incorporated by reference herein.

Suitable selectable markers for selection in plant cells include, but are not limited to, antibiotic resistance genes, such as, kanamycin (nptII), G418, bleomycin, hygromycin, chloramphenicol, ampicillin, tetracycline, and the like. Additional selectable markers include a bar gene which codes for bialaphos resistance; a mutant EPSP synthase gene which encodes glyphosate resistance; a nitrilase gene which confers resistance to bromoxynil; a mutant acetolactate synthase gene (ALS) which confers imidazolinone or sulphonylurea resistance; and a methotrexate resistant DHFR gene.

The particular marker gene employed allows for selection of transformed cells as compared to cells lacking the DNA which has been introduced. Preferably, the selectable marker gene is one which facilitates selection at the tissue culture stage of the molecular switch methods of the invention, e.g., a hygromycin phosphotransferase, kanamyacin or ampicillin resistance gene.

By way of example, a generalized plasmid (pAG-2170), suitable for use in Agrobacterium-mediated plant transformation finds utility in practicing the invention, as described in Example 3.

Briefly, plasmids comprising modified RBDV genes were inserted into the multiple cloning site of the pAG2170 binary vector between the CsVMV promoter and the NOS terminator as illustrated in FIG. 6. The exemplified plasmids were designed to include the coding sequence for the wild type RBDV coat protein, the wild type RBDV movement protein and 4 different mutant RBDV movement proteins, respectively as summarized below in Table 1. (See also FIG. 6.)

TABLE 1

Exemplary Plasmids Comprising RBDV Genes

| Plasmid name | Modified RBDV gene |
| --- | --- |
| pAG-2171 (M1) | Non-translatable MP start codon removed, 2 stop codons added at amino acid residues 3 and 6 |
| pAG-2172 (M2) | Deletion of codons 2–6 of MIP |
| pAG-2173 (M3) | Deletion of codons 5–14 of RBDV MP |
| pAG-2174 (M4) | Deletion of codons 37–42 of RBDV MP |
| pAG-2177 | RBDV MP, wild type |
| pAG-2178 | RBDV CP, wild type |

In the exemplary plasmids, the various RBDV coding sequences are under the transcriptional control of the 35S promoter of CsVMV (cassava vein mosaic virus; Verdaguer et al., 1998) and the selectable marker gene hpt is under the regulatory control of the RE4 promoter.

V. Developing Resistance to RBDV In Transgenic Plants

Transgenic raspberry plants, plant cells, and methods for making and using them according to the present invention find utility in increasing the yield of fruit from raspberry plants. In one aspect, the invention provides a RBDV-resistant raspberry plant comprising plant cells transformed with a nucleic acid construct comprising a modified RBDV-encoding nucleic acid, such that the transformed raspberry plant and plant cells have increased resistance to infection by the virus relative to a wild type raspberry plant which is free of such transformed cells.

A. Transforming Plants with Agrobacterium

Vectors useful in the practice of the present invention may be introduced into plant cells by any of the numerous methods routinely used by those of skill in the art to produce transgenic plants.

For example, vectors may be microinjected directly into plant cells by mechanical transfer of the nucleic acid construct or cassette (Crossway, 1985), or the nucleic acid construct or cassette may be transferred into a plant cell using polyethylene glycol (Krens et al., 1982). High velocity biolistic penetration by small particles with the nucleic acid either within a matrix of small beads or particles, or on the surface of such small beads or particles may also be used for introduction of nucleic acid sequences into plant cells. (See, e.g., Klein et al., 1987; Knudsen et al., 1991). Yet another method for introduction of nucleic acid sequences into plant cells is fusion of protoplasts with other entities, either minicells, cells, lysosomes or other fusible for introduction of nucleic acid segments into plant cells with lipid surfaces (Fraley et al., 1982).

A preferred method for introduction of a nucleic acid construct or cassette into the plant cells is electroporation (From et al., 1985). In this technique, electrical impulses of high field strength reversibly permeabilize biomembranes allowing the introduction of plasmids into plant cells or protoplasts.

Another preferred method of introducing a nucleic acid construct comprising a sequence of interest into plant cells is to infect a plant cell, explant, meristem or seed with Agrobacterium, in particular *Agrobacterium tumefaciens.* A nucleic acid construct comprising a sequence of interest is introduced into appropriate plant cells, by means of the Ti plasmid of *Agrobacterium tumefaciens.* The Ti plasmid is transmitted to plant cells upon infection by *Agrobacterium tumefaciens,* and is stably integrated into the plant genome (Horsch et al., 1984; Fraley et al, 1983; and Schell, 1987).

In one aspect of the invention, an Agrobacterium binary plant transformation vector is introduced into a disarmed strain of *A. tumefaciens* by electroporation (Nagel R. et al., 1990), followed by co-cultivation with plant cells, resulting in transfer of the heterologous nucleic acid construct(s) into plant cells. Upon infection by *Agrobacterium tumefaciens,* a heterologous DNA sequence is stably integrated into the plant genome in one or more locations.

In a further aspect of the invention, transgenic plants are produced using Agrobacterium T-DNA vectors or microprojectile bombardment, where a heterologous nucleic acid coding sequence is integrated into the plant genome and traditional breeding is used to generate transgenic seed stock and transgenic plants.

As further described in Example 4, leaves and petiole explants of in vitro propagated raspberry cultivar Meeker, were co-cultivated with *Agrobacterium tumefaciens,* primary shoot regenerants isolated and taken through an iterative culture process to develop homogeneous clones of raspberry plants.

B. Regeneration and Resistance Testing of Transgenic Plants

Transformed explant cells are screened for the ability to be cultured in selective media having a threshold concentration of a selective agent, e.g., hygromycin. Explants that can grow in or on the selective media are transferred to a fresh supply of the same media and cultured again. The explants are then cultured under regeneration conditions to produce regenerated plant shoots. Primary shoot regenerants on selection medium are chimeral and are typically taken through an iterative culture process to eliminate non-transformed cells. See e.g., co-owned U.S. Ser. No. 09/177,758, (now U.S. Pat. No. 6,127,182) expressly incorporated by reference herein. Homogenously transformed shoots are induced to root on medium with selection followed by outplanting to soil. Plants may then be grown to provide seed, cuttings, or the like for propagating the transformed plants. The method provides for high efficiency transformation of plant cells with expression of modified native or non-native plant genes and regeneration of transgenic plants, as further detailed in Examples 4 and 5.

After rooting and establishment in soil, transgenic plants were challenge-inoculated by bud grafting with RBDV infected raspberry plants. Results indicate that the transgenic plants are resistant to RBDV infection. When transformed with pAG-2171, pAG-2172, pAG-2173 or pAG-2174, which comprise the nucleic acid sequence encoding a non-translatable movement protein, a movement protein coding sequence wherein codons 2–6 are deleted, a movement protein coding sequence wherein codons 5–14 are deleted, or a movement protein coding sequence wherein codons 37–42 are deleted, respectively, 35%, 61%, 26% and 35% of the plants that were challenged with RBDV two separate times, remained free of RBDV infection at least 3 months after grafting. (See Example 5.)

VI. Methods of Detecting Raspberry Bushy Dwarf Virus (RBDV) Infection

Diagnostic methods for detecting RBDV infection in specific plant samples, and for detecting levels of expression of RBDV in plant tissues by use of the sequences described herein, also form part of the invention. Methods for detecting mutations in the coding region of a coat or movement protein of RBDV are also contemplated.

A. Immunoassay

Immunological tests, such as ELISA, have been developed for the detection of RBDVs. (See Example 4 and Martin, 1998.)

Techniques for carrying out such immunoassays are generally known, and include ELISA, Immunogold labeling, Western Blot and immunodotblot, as well as IC-PCR. Such procedures are generally described in Harlow et al., 1988 and Hu et al., 1990.

B. PCR

Reverse transcriptase polymerase chain reaction (RT-PCR) and immunocapture reverse transcription polymerase chain reaction (IC-RT-PCR) may also be used for detection of RBDV infection in raspberry plants. (See, e.g., Kokko et al., 1996.)

As is known to those of skill in the art, PCR refers to a process of amplifying one or more specific nucleic acid sequences, by (i) annealing oligonucleotide primers to a single-stranded nucleic acid template in a test sample, (ii) combining the product of (i) with a nucleic acid polymerase to extend the 3' ends of the annealed primers and thereby form a double-stranded nucleic acid product, (iii) denaturing the double-stranded nucleic acid product to yield two single-stranded nucleic acids, and (iv) repeating the steps of primer annealing, primer extension, and product denaturation enough times to generate detectable amounts of amplified sequences defined by the primers. The sequential annealing, extension and denaturation steps are controlled by varying the temperature of the reaction container, normally in a repeating cyclical manner. Annealing and extension are typically carried out between 40–80° C., whereas denaturation requires temperatures between about 80 and 100° C.

A polymerase chain reaction (PCR) reaction mixture generally includes the components necessary for amplification of specific nucleic acid sequences. Kits and reagents for carrying out PCR reactions are commercially available and generally include nucleotides, (some or all of dCTP, dATP, dGTP and dTTp or dUTP), one or more of which may be labeled in any known or suitable manner, e.g., radio labeled, the polymerase, and one or more of buffers, salts, stabilizing agents and reagents for nucleic acid extraction and detection. (See, e.g. products available from Perkin-Elmer.)

A plant extract sample for use in a PCR assay for RBDV sequences may be prepared using Quiagen's RNAeasy plant RNA extraction kit protocol, with modifications (MacKenzie et al, 1996; Example 1). Viral RNA is isolated and converted into cDNA, which is used in the assay.

In some cases, preliminary purification of RBDV virus particles or viral RNA is not necessary, i.e., for IC-RT-PCR (Kokko et al., 1996). In such cases, virus is enriched using antibodies bound to microplate wells, followed by lysis of the viral particles, and RT-PCR of the viral RNA.

It will understood by those of skill in the art that any of a number of PCR primer sets may be designed and used for the detection of RBDV nucleic acids, based on the wild type RBDV coat and movement protein encoding nucleic acid sequences provided herein.

C. Others

An assay for RBDV infection in raspberry may also involve obtaining total mRNA from the tissue and detecting and/or quantitating the mRNA in the sample by methods known to those of skill in the art, such as Northern blot analysis.

Either the cloned wild type RBDV coat and movement protein encoding nucleic acid sequences or sequence information from the RBDV coding sequences may be used to detect sequences having a high degree of sequence similarity or identity to the entire coding sequence or a fragment thereof. Such sequences can be isolated, e.g., from a selected cDNA library by hybridization under high stringency conditions, as defined above. As is known in the art, hybridization is typically performed by designing a polynucleotide probe derived from the target sequence, labeling the probe with reporter moieties, and using the reporter-labeled probe to visualize the presence of similar sequences immobilized on a solid support. The probe can be labeled using any of a variety of reporter molecules known in the art and detected accordingly: for example, radioactive isotopic labeling and chemiluminescent detection reporter systems (Tropix; Bedford, Mass.).

The labeled probes may be hybridized to samples being tested using standard hybridization procedures. Typically, the polynucleotide sample (e.g., mRNA) is immobilized or "blotted" onto a nylon or nitrocellulose membrane (available, e.g., from Schleicher & Schuell, Keene, N.H.). Variations of such blots include filters lifted from media (e.g., agar) plates containing a library, Northern blots, dot blots and slot blots. The membranes containing the immobilized polynucleotides are washed in a pre-hybridization solution and incubated at a controlled temperature in a hybridization solution containing the probe. Following hybridization, the membranes are washed under conditions effective to result in the desired degree of hybridization specificity following standard methods (e.g., Ausubel et al., 1993; Sambrook et al., 1989).

High stringency hybridization conditions are well known in the art and further described above.

The presence of RBDV proteins or polypeptides can also be evaluated by Western blot or ELISA using antibodies specific for the particular strain of RBDV, as detailed above.

VII. Utility of RBDV Sequences in the Generation of RBDV Resistant Plants

The RBDV coat and movement protein-encoding polynucleotides of the present invention may be used for a variety of purposes. The polynucleotides may be used to detect and quantitate expression of RBDV in plant tissue prior to use in vegetative propagation, by detecting the presence of RBDV RNA.

More importantly, wild type RBDV coat protein or movement protein coding sequences and mutants thereof may be used to generate RBDV resistant raspberry plants. In the case of mutants, RBDV coding sequences which have been modified in a manner effective to result in a defective sequence are constructed, e.g., by eliminating the start codon or incorporation of multiple stop codons to produce a non-functional or untranslated movement or coat protein. When plants are transformed with a nucleic acid construct containing such wild type or mutant RBDV coding sequences, the plants may become resistant to RBDV infection. As suggested by the examples provided herein, plants transformed with a plant expression vector containing such RBDV coat protein or movement protein coding sequences are resistant to infection by RBDV and other related or unrelated strains of RBDV. RBDV-resistant raspberry plants are particularly useful in producing an increased yield of commercially useful raspberry fruit from RBDV-susceptible cultivars of raspberry.

The following examples illustrate, but are in no way intended to limit the scope of the present invention.

Standard recombinant DNA techniques were employed in all constructions, as described in Adams et al. S.F., *Plant Physiology* 70:117–123 (1977); Ausubel, F M, et al., in CURRENT PROTOCOLS IN MOLECULAR BIOLOGY, John Wiley and Sons, Inc., Media, Pa. (1992); Hooykaas, P J, and Schilperoot, R A, in TRENDS IN BIOCHEMICAL SCIENCES, International Union of Biochemistry and Elsevier Science Publishers, v.10(8):307–309 (1985); and Sambrook J, et al., in MOLECULAR CLONING: A LABORATORY MANUAL, Cold Spring Harbor Laboratory Press, Cold Spring Harbor, N.Y., Vol. 2 (1989), each of which is expressly incorporated by reference herein.

EXAMPLE 1

Cloning and Sequencing of RBDV Open Reading Frames (ORFs)

A. Virus Isolate and RNA Preparation

RBDV was isolated from the *Rubus idaeus* clone OSU769 (purified from mechanically inoculated *Chenopodium quinoa*), 10–14 days after inoculation. Virus was purified using the protocol described by MacDonald et al., 1991 for purification of blueberry shock ilarvirus. RNA was extracted from purified virus with phenol:chloroform:isoamyl alcohol (25:24:1) and stored at –80° C.

B. Cloning and Sequencing of RBDV Coat Protein ORF

Oligonucleotides RBDVCP3' (SEQ ID NO:5) and RBDVCP5' (SEQ ID NO:6) were used as the primers for reverse transcription with RBDV-RNA2. Oligonucleotide RBDVCP3' has an XbaI site (indicated below as bolded) and 2 extra bases at the 5' end with 24 bases homologous to the 3' end of the RBDV coat protein ORF (Natsuaki et al., 1991) Oligonucleotide RBDVCP5' has an XbaI and NcoI site at the 5' end, a start codon indicated as underlined and includes 23 of 24 3' nucleotides that are identical to the 5' end of the coat protein (CP) of RBDV. In RBDVCP5' the codon for the second amino acid has been changed from a serine to an alanine to create an NcoI site, with the changed nucleotide indicated as lower case. RBDVCP5' together with RBDVCP3' was used to amplify the coat protein gene of RBDV in a standard PCR reaction.

```
RBDVCP3' 5' CCT CTA GAC TAA GTT AGA ACT ATT GTG GAG GA 3'     (SEQ ID NO:5)

RBDVCP5' 5' CCT CTA GAC CAT GgC GAA GAA AGC TGT TCC ACC A 3'  (SEQ ID NO:6)
```

The PCR product was digested with XbaI and cloned into Bluescript KS+ previously digested with XbaI and treated with calf intestinal phosphatase (CIP). The cloned product was sequenced by dideoxy sequencing at the Central Services Laboratory at Oregon State University. A primer in each orientation midway in the coat protein gene was designed after the first sequencing reactions and a second reaction carried out using these primers to complete the sequencing in both directions.

C. Preparation of the Coat Protein Construct for Transformation into *Agrobacterium tumefaciens*

The Bluescript KS+ plasmid containing the coat protein (CP) open reading frame (ORF) was digested with XbaI and Acc65I and gel purified. The pAG2170 plasmid was cut with XbaI, dephosphorylated, gel purified and then digested with Acc65I and gel purified again. The CP insert was then cloned into an XbaI and ACC65I digested pAG2170 plasmid. Colonies were miniprepped, digested and checked for orientation. DNA from a single colony with the insert in the right orientation was used for transformation into *Agrobacterium tumefaciens* and subsequent transformation of red raspberry cv. Meeker.

D. Cloning and Sequencing of the Movement Protein ORF of RBDV

Oligonucleotide RBDVMP3' (SEQ ID NO:7) and RBDVMP5' (SEQ ID NO:8) were used as the primers for reverse transcription with RBDV-RNA2. RBDVMP3' has a HindIII site (underlined), plus 6 extra bases at the 5' end and 21 bases homologous to the 3' end of the coat protein ORF (Natsuaki et al., 1991). Oligonucleotide RBDVMP5' has an XbaI site (underlined) at the 5' and 18 bases identical to the 5' end of the RBDV movement protein ORF. RBDVMP3' and RBDVMP5' were used to amplify the movement protein gene of RBDV in a standard PCR reaction.

```
RBDVMP3' 5' CCC ACG AAG CTT TTA ATA AAC GGA ATG TGA AGG 3'  (SEQ ID NO:7)

RBDVMP5' 5' TGC TCT AGA ATG TTT AGC AGA AGT TCC 3'          (SEQ ID NO:8)
```

The PCR product was digested with XbaI and HindIII and cloned into Bluescript KS+ previously digested with XbaI and HindIII. The cloned product was sequenced by dideoxy sequencing from both ends using universal forward and reverse primer at the Central Services Laboratory at Oregon State University. Primers were then made, so that the sequencing could be extended in each orientation. This process was repeated three times until the MP gene was completely sequenced in both directions.

EXAMPLE 2

Modified RBDV Proteins

A. Development of Modified RBDV Proteins

Four primers were designed to make mutations in the MP of RBDV. Mutagenesis primer RBDVM1 (SEQ ID NO:9); depicted with the altered nucleotides underlined), changes the start codon, ATG to AGG, and introduces two stop codons by changing amino acid codons at position 3 and 6 to stop codons. The XbaI site at the 5' end is retained and an internal DraI site is introduced for easy screening of mutants. RBDVM2 (SEQ ID NO:10) deletes amino acids 2 through 6. RBDVM3 (SEQ ID NO:11) deletes amino acids 5 through 14. RBDVM4 (SEQ ID NO:12) deletes amino acids 37–42.

```
RBDVM1 5' GGC CGC TCT AGA AGG TTT TAA AGA AGT TAA TCT ACT CGC AGC TCC C 3'  (SEQ ID NO:9)

RBDVM2 5' GGC CGC TCT AGA ATG TCT ACT CGC AGC TCC CTT G 3'                   (SEQ ID NO:10)

RBDVM3 5' CGC TCT AGA ATG TTT AGC AGA AGC AGG AGT GGC TCC 3'                 (SEQ ID NO:11)

RBDVM4 5' CTG TGA GGG GGT TGT CTG GAG GAT TAG CTT GGG CC 3'                  (SEQ ID NO:12)
```

The template for the design of all four mutants was the RBDV MP ORF sequence cloned into Bluescript KS+ and sequenced as described above. Single-stranded DNA was prepared and mutagenesis carried out as per Kunkel (1987). The mutagenesis oligonucleotides were each annealed to an aliquot of the ssDNA, extended using T4 DNA polymerase and ligated using T4 DNA ligase. The resulting plasmids were transformed into TOP cells (Invitrogen, Carlsbad, Calif.). Colonies were checked for inserts and ssDNA prepared from two colonies for each mutant. The ssDNA was sequenced at the Central Services Laboratory at Oregon State University. At least one clone that was sequenced from each mutant had the desired mutation and was cloned into the binary vector pAG2170.

B. Preparation of Movement Protein Constructs for Transformation into *Agrobacterium tumefaciens*

The Bluescript KS+to plasmids containing the MP ORF and each of the mutant plasmids were digested with XbaI and HindII and gel purified. The pAG2170 plasmid was cut with Acc65I, filled in with Klenow and the enzymes inactivated by heating at 75° C. for 10 min. The plasmid was then cut with XbaI and gel purified. The MP inserts were then cloned into an XbaI and ACC65I digested pAG2170 plasmid. Colonies were miniprepped and digested to check for orientation. DNA from a single colony for each mutant with the insert in the right orientation was used for transformation into *Agrobacterium tumefaciens* and subsequent transformation of red raspberry cv. Meeker.

EXAMPLE 3

Plasmid Constructs for Introduction into Raspberry

A generalized plasmid was made which was suitable for use in Agrobacterium-mediated plant transformation and which would accept various sequences from RBDV. The generalized plasmid, pAG-2170, was assembled using: the 10 kb BamHI-SacI fragment from pGPTV-Kan (Becker, et.al., 1992), a 1.3 kb fragment consisting of a constitutive promoter, the raspberry E4 promoter (RE4 pro) driving the expression of the hygromycin transferase gene (hpt), and a 0.6 kb PCR amplified fragment of the Cassava Vein Mottle Virus 35S promoter (CsVMV pro, Verdaguer et al., 1998) upstream of a multiple cloning site.

The 10 kb BamHI-SacI fragment from pGPTV-Kan (Becker et al., 1992) provided the necessary instructions for plasmid replication and selection in *E. coli* and Agrobacterium, the right and left borders necessary for Agrobacterium-mediated plant transformation and the NOS and Gene 7 (g7) terminators that terminate the RBDV and hpt genes respectively.

The raspberry E4 promoter was acquired by screening a genomic raspberry lambda library with the tomato E4 gene (Lincoln et al 1988). The raspberry E4 promoter facilitates constitutive expression and was used to drive the antibiotic resistance gene for expression in plants.

The hpt gene, under the control of RE4 promoter and terminated by the g7 terminator, provides antibiotic resistance in transformed plants. The CsVMV promoter which also directs constitutive expression in plants was cloned from the Cassava Vein Mottle Virus (Roger Beachy's lab at the Scripps Institute).

EXAMPLE 4

Preparation and Characterization of Transigenic Raspberry Plants

Various plasmids comprising modified RBDV genes were inserted into the multiple cloning site of the pAG-2170 binary vector between the CsVMV pro and the NOS terminator. (FIG. 6, Table 2) The various binary vectors containing RBDV genes were transformed into *Agrobacterium tumefaciens* strain EHA105 containing the disarmed supervirulent plasmid pTiBo542 in the C58 chromosomal background (Hood et al., 1993).

TABLE 2

Heterologous Nucleic Acid Constructs Containing RBDV Genes.

| Plasmid Name | Modified RBDV Coding Sequence |
|---|---|
| pAG-2171 (M1) | FIG. 5A; SEQ ID NO:13 |
| pAG-2172 (M2) | FIG. 5B; SEQ ID NO:14 |
| pAG-2173 (M3) | FIG. 5C; SEQ ID NO:15 |
| pAG-2174 (M4) | FIG. 5D; SEQ ID NO:16 |
| pAG-2177 (RBDV MP, wild type) | FIG. 2; SEQ ID NO:3 |
| pAG-2178: (RBDV CP, wild type) | FIG. 1; SEQ ID NO:1 |

A. Transformation of raspberry, cv Meeker.

Leaves and petioles were excised from proliferating shoot cultures maintained on modified MS medium (Murashige et al., 1962) supplemented with 1 mg/l BA and gelled with 0.2% phytagel. Petioles were cut into 4–6 mm segments. Leaf blades 4–5 mm in length were used as whole explants or they were cut into transverse halves when blades greater than 6 mm in size were used. Leaf explants were cultured with the adaxial surface in contact with the medium.

B. Co-cultivation of explants with Agrobacterium.

A freshly grown single colony of *Agrobacterium tumefaciens* was inoculated into 30 ml of mg/l (Garfinkel and Nester, 1980) liquid medium supplemented with 50 mM acetosyringone, pH 5.6, was grown on a shaker at 200 rpm overnight (16–18 hrs). The bacterial suspension had an average count of 0.5–0.6×$10^9$ cells/ml at the start of co-cultivation with plant tissues. Soon after excision, the petioles and leaf explants were soaked in the Agrobacterium suspension. After 30–60 minutes, they were transferred to flasks containing liquid MS medium (Murashige et al., 1962) and kept on a shaker at 100 rpm. The density of explants was approximately 100 to 120 segments in about 30 ml of medium in 125 ml flasks. After 2 days of co-cultivation, the explants were rinsed with liquid medium, blotted and plated on regeneration medium containing hygromycin selection.

C. Tissue culture media and growth conditions.

Shoot regeneration medium consisting of modified MS medium supplemented with IBA 0.1 mg/l, 0.1–1.0 mg/l TDZ and 3% D-glucose/sucrose as the carbon source was prepared and the pH adjusted to 5.8 before gelling with 0.2–0.25% phytagel. Regeneration medium was prepared containing antibiotics carbenicillin (500 mg/l) and hygromycin at varying levels (5–20 mg/l), depending on the responses of initial explant. The culture medium was autoclaved at 120° C. at 1.1 kg. $cm^{-2}$ except for the antibiotics which were filter sterilized. Cultures were kept at 25° C. with 16-hr photoperiod provided by white fluorescent light at an average intensity of 50 $\mu$mol $m^{-2}s^{-1}$. Observations were recorded every 3–4 weeks and cultures transferred to fresh medium of the same composition with appropriate changes in the level of antibiotics. Soon after co-cultivation the explants received the lowest level of selection mentioned above, and as the explants underwent proliferation in culture, the selection level was gradually increased based on the rate of dedifferentiated tissue on the explant. The selection level during the period of selecting transgenics ranged from 6–15 mg/l hygromycin depending on the stage of development.

Putatively transformed shoot regenerants were isolated and cultured on shoot proliferation medium with selection at 12–15 mg/l of hygromycin. Rooting medium for transgenic shoots contained half strength MS (Murashige et al., 1962) or Anderson's Salts (Anderson, 1980), MS vitamins, supplemented with 3% D-glucose/sucrose, 0.05 mg/l IBA, 200–300 mg/l carbenicillin/ timentin and 8–10 mg/l hygromycin. Leaf, petiole and nodal explants were cultured in petri plates with 40 ml of regeneration/proliferation medium. From 6 to 9 shoot explants for multiplication/ rooting were cultured on phytatrays with 120 ml of proliferation or rooting medium.

D. Treatment of primary shoot regenerants and recovery of transgenic clones.

Primary shoot regenerants on selection medium contained both transformed and non-transformed cells (i.e., they were chimeric). Non-chimeric transgenic clones were developed by iterative culture of petiole, node and leaf explants, on selection medium, using successive generations of shoots derived from the primary regenerants. Primary shoot regenerants were isolated and cultured on shoot proliferation medium containing 12–20 mg/l hygromycin. Leaves, petioles and nodal segments were isolated from the shoots which withstood selection, and cultured on regeneration medium with 12–20 mg/l of hygromycin. This iterative process of reculture of excised tissues from regenerants was continued until no part of the shoots necrosed or bleached under selection pressure. Shoots were considered fully transformed only after they passed the above criteria (Mathews et al., 1995; Mathews et al., 1998). Such shoots were multiplied on proliferation medium for generating clonal plants from each independent transformation event.

E. Establishment Of Transgenic Shoots/Plants In The Green House.

Individual shoots were separated from tissues with profusely proliferating shoots when grown on selection medium, and isolated for root induction. Phytatrays with rooted plants were kept in a greenhouse with loosened lids for 2–4 days, followed by transfer to soil following rinsing with water to remove the media.

F. Validation of transgenic events.

Random samples of the transgenic plants from each construct were evaluated to confirm the presence of the hpt transgene using standard protocols for Southern hybridization. DNA was extracted using the CTAB extraction protocol of Doyle et al., 1990. Single and double digested DNA was transferred to Nytran membranes followed by hybridization with a $^{32}P$ labeled or digoxin-labeled hpt or RBDV probe. Each blot was washed and exposed to a storage phosphor screen and scanned on a Storm 840 Scanner (Molecular Dynamics) to confirm the stable integration of a given transgene into the raspberry genome.

G. Evaluation Of RBDV Resistance By Graft Inoculation In Greenhouse.

Transgenic plants were grown in a green house at the USDA-ARS Horticultural Crops Research facility in Corvallis, Oreg. Two plants of each transformant were grafted with two buds from RBDV-infected 'Meeker' raspberry. Plants were tested for the presence of RBDV by ELISA after they had been grafted. The ELISA tests were performed as described previously (Martin, 1998).

Fifty individual transformants were generated for each of the above constructs. The presence of transgene was confirmed by Southern hybridization in a random sample of leaf tissues from various transgenic plants. Twenty-five plants of each transformant were propagated in tissue culture for evaluation and field trials. Two plants of each construct were potted into 6 inch pots and grown in a greenhouse for grafting.

EXAMPLE 5

Evaluation of Transgenic Raspberry Plants in Field Trials

A. Transformed Plants in the Field

Transgenic plants grown in a green house at the USDA-ARS Horticultural Crops Research facility in Corvallis, Oreg. were used to establish field trials in northern Washington. Three replicates of three plant plots for each of the constructs shown in Table 2, with the exception of pAG-2177 were used to set up field trials at the northern Washington site. The disease pressure at this site is extreme because a larger plot of 'Meeker' raspberries that are known 100% positive for RBDV surrounds the experimental plot. A single replicate of three plant plots was also established at the North Willamette Research and Extension Center location in Aurora, Oreg. Table 3 lists the number of transformed events established at each field site.

TABLE 3

| Number and Location of Transformants in the Field | | |
|---|---|---|
| Construct | Northern Washington # transformants/3 replicates | NWREC, Aurora Oregon # transformants/1 replicates |
| pAG2171 | 42 | 48 |
| pAG2172 | 31 | 38 |
| pAG2173 | 35 | 44 |
| pAG2174 | 42 | 43 |
| pAG2178 | 29 | 51 |
| Totals | 179 | 225 |

B. Grafting and Evaluation of Resistance to RBDV

Transgenic plants representing each of the constructs shown in Table 3 were challenged with RBDV by approach grafting at the bud from known RBDV-infected 'Meeker' raspberry plants. Immediately after the graft was put in place grafted plants were transferred to a mist room where they were frequently watered for several days. 182 transgenic raspberry plants were grafted in June 2000. In October 2000, 152 of those 182 were re-grafted. After at least one month from the time of grafting each transgenic plant was tested for presence of RBDV by ELISA to determine if it was susceptible to infection by the virus. The ELISA tests were performed as previously described (Martin, 1998).

C. Confirmation of Transgene Presence by RT-PCR

RT-PCR was performed on a sample of RBDV resistant transgenic plants in order to confirm the presence of the transgene. The youngest available leaf tissue was collected from randomly selected transgenic plants containing each individual construct shown in Table 3, and used for RT-PCR analysis. Collected tissue was immediately frozen in liquid nitrogen and stored in individual 50 ml collection tubes in a cooler filled with dry ice. A total of 28 tissue samples were transferred to a −80° C. freezer for storage until RNA extraction (Table 4). RNA was extracted from transgenic and non-transgenic plants as previously reported (Chang et al. 1993).

TABLE 4

| Number of tissue samples collected for RT-PCR | |
|---|---|
| Construct | Tissue Samples Collected |
| pAG2171 | 5 |
| pAG2172 | 5 |
| pAG2173 | 5 |
| pAG2174 | 5 |
| pAG2177 | 3 |
| pAG2178 | 5 |
| Totals | 28 |

DNAse digestion of RNA samples was carried out to remove any remaining genomic DNA using the following protocol.

5× DNAse digestion buffer (100 μl 50 mM Tris, pH 8.0; 15 μl 30 mM $MgCl_2$; 5 μl 50 mM NaCl and RNase free $H_2O$ up to 500 μl) was prepared and 15 μl added to the Master mix for each reaction. In each reaction, 50 μl RNA, 15 μl 5× DNase digest buffer (Promega), 2.5 μl RNase free DNAse (Promega), 0.5 μl RNasin Ribonuclease Inhibitor (Promega) and 7 μl water was combined for a total of 75 μl (Master mix).

In carrying out the procedure, 25 μl of Master mix is added to each tube together with 50 μl RNA, the mixture is vortexed and incubated at 37° C. for 30 minutes, extracted with phenol/chloroform, then chloroform, precipitated with 0.2 vol. 5M $NH_4Oac$ and 2.5 vol. EtOH, followed by centrifugation for 30 minutes at the highest speed in a microcentrifuge at 4° C., and the pellet was resuspended in RNase free $H_2O$.

Following DNase digestion, a negative control PCR reaction using Taq DNA polymerase (Promega) was performed by standard methods as described below, to ensure that all genomic DNA had been eliminated from the RNA samples before RT-PCR was conducted.

PCR was performed by standard methods (Sambrook, et al. 1989) under the following thermocycler conditions: 94° C. for 5 min, followed by 30 cycles of: 94° C. for 30 seconds, 60° for 30 seconds, 72° C. for 1 minute and 72° C. for 2 minutes, using Taq DNA polymerase (Promega), 10× PCR Buffer (Promega) and a Stratagene Robocycler Gradient 96 thermocycler.

The process of cDNA synthesis and subsequent PCR of transgenic RNA was carried out using a modified from of the protocol described by MacKenzie et al., 1997, using the reagents provided in Table 5. In carrying out cDNA synthesis, master mixes were prepared for the desired number of reactions plus an $H_2O$ control. 14.65 μl of master mix 1 was aliquoted into Ultra Thin-Walled PCR reaction tubes (Island Scientific), 1 μg RNA was added together with water to a final volume of 19.65 μl and the mixture heated at 97° C. for 5 minutes, cooled on ice, then centrifuged to collect condensation. Then 30.35 μl of master mix 2 was aliquoted into the reaction tubes, the components mixed, centrifuged, incubated at 42° C. for 1 hour, heated at 99° C. for 10 minutes, then cooled on ice.

TABLE 5

| cDNA synthesis reagents | | | |
|---|---|---|---|
| Master Mix 1 | | Master Mix 2 | |
| | per 1 rxn. | | per 1 rxn. |
| Water | 13.65 μl | 5x buffer (Promega) | 10 μl |
| Random primer | 1 μl | 100 mM DTT (Promega) | 9.8 μl |
| | | 10 mM dNTP (Promega) | 2.6 μl |
| | | RNAsin (Promega) | 1.6 μl |
| | | Rtase (Promega) | 1 μl |
| | | BSA (Promega) | 0.35 μl |
| | | Water | 5 μl |

PCR was the carried out using 5 μl 10× PCR buffer (Promega), 5 μl 25 mM MgCl (Promega), 0.5 μl 100 μM 5' primer (GibcoBRL), 0.5 μl 50 μM 3' primer (GibcoBRL), 1 μl 10 mM dNTP (Promega), 0.5 Amplitaq (Promega), and 32.5 μl water for a total volume of 45 μl. The PCR reaction was allowed to proceed under the following conditions: 94° C. for 2 min, followed by 30 cycles of: 94° C. for 30 seconds, 60° C. for 30 seconds, 72° C. for 1 minute and 72° C. for 2 minutes.

Additionally, RT-PCR of RNA extracted from non-transgenic raspberry leaf tissue was performed as a negative control. Primers used for RT-PCR and PCR were targeted to transgenes and CsVMV, as provided in Table 6. PCR products were evaluated following electrophoresis on 1%–1.2% agarose gels prepared with 1× TAE and 25 μg/ml EtBr.

TABLE 6

Primers used for RT-PCR and PCR of samples by construct

| Construct | 3' primer | Sequence | 5' primer | Sequence |
|---|---|---|---|---|
| pAG2171<br>pAG2172<br>pAG2173<br>pAG2174<br>pAG2177 | CsVMVp3'F[1] | 5'_GTGTAAGCTATT TTCTTTGAAGTA_3' | RBDVMP[2] | 5'_TACTTCTTAAATTC CTTAAATTTGTTG_3' |
| pAG2178 | CsVMVp3'F | 5'_GTGTAAGCTATT TTCTTTGAAGTA_3' | RBDVCP[2] | 5'_TTTAAACCCGAAA CAAGATTTATG_3' |

[1]Manufactured by Promega
[2]Manufactured by GibcoBRL

D. RT-PCR of RBDV Resistant Transgenic Plants

One month after a single RBDV challenge, 164 of the 182 plants grafted were found to test negative for RBDV. One month after a second RBDV challenge to 152 of those 164 transgenic plants that originally tested negative for the virus, 38% remained free from RBDV infection. Table 7 lists by construct the percentage of plants that remain resistant to infection by RBDV after being twice challenged with the virus.

TABLE 7

Transgenic Plants that remained resistant To RBDV after Two Challenges with Virus

| Construct | n = | % resistant in November 2000 |
|---|---|---|
| pAG-2171 | 34 | 35% |
| pAG-2172 | 28 | 61% |
| pAG-2173 | 31 | 26% |
| pAG-2174 | 7 | 35% |
| pAG-2178 | 26 | 57% |
| Totals | 152 | 38% |

RT-PCR of transgenic raspberry plants that remained resistant to RBDV after two challenges with the virus confirmed the presence of the respective transgene in each of the samples tested. The RT-PCR results demonstrated that the majority of plants transformed with RBDV movement protein-based constructs (pAG-2171, pAG-2172, pAG-2173, pAG-2174, and pAG-2177) and with an RBDV coat protein-based construct (2178) were positive by RT-PCR when amplified with a primer pair specific to CsVMV and the respective RBDV coding sequence as shown in Table 8.

PCR of the RNA samples with Taq DNA polymerase did not amplify any DNA fragments, confirming that the 28 RNA samples used for RT-PCR were free of genomic DNA.

TABLE 8

Results of PCR of RT synthesized cDNA

| Contents | Primers | RT-PCR[1] positives | Contents | Primers | RT-PCR[1] positives |
|---|---|---|---|---|---|
| PAG2171 samples | CsVMVp3'F RBDVMP (5') | 5/5 (s) | pAG2177 samples | CsVMVp3'F RBDVMP (5') | 3/3 (s) |
| PAG2172 samples | CsVMVp3'F RBDVMP (5') | 4/5 (w) 1/5 (s) | non-trans-formed tissue | CsVMVp3'F RBDVMP (5') | 0/1 |
| PAG2173 samples | CsVMVp3'F RBDVMP (5') | 1/5 (w) 4/5 (s) | $H_2O$ control | CsVMVp3'F RBDVMP (5') | 0/1 |
| PAG2174 samples | CsVMVp3'F RBDVMP (5') | 1/5 (w) 4/5 (s) | pAG2178 samples | CsVMVp3'F RBDVCP (5') | 1/5 (w) 4/5 (s) |
| | | | non-trans-formed tissue | CsVMVp3'F RBDVCP (5') | 0/1 |
| | | | $H_2O$ control | CsVMVp3'F RBDVCP (5') | 0/1 |

[1](s) = strongly positive band on ethidium bromide stained gel containing PCR products following electrophoresis
(w) = weakly positive band on ethidium bromide stained gel containing PCR products following electrophoresis

TABLE 9

Sequence Listing Table

| DESCRIPTION | SEQ ID NO |
|---|---|
| nucleotide sequence which encodes RBDV coat protein (FIG. 1) | 1 |
| predicted amino acid sequence for RBDV coat protein (FIG. 3) | 2 |
| nucleotide sequence which encodes RBDV movement protein (FIG. 2) | 3 |
| predicted amino acid sequence for RBDV movement protein (FIG. 4) | 4 |
| RBDVCP3' primer for cloning RBDV coat protein gene 5' CCT CTA GAC TAA GTT AGA ACT ATT GTG GAG GA 3', | 5 |
| RBDVCP5' primer for cloning RBDV coat protein gene 5' CCT CTA GAC CAT GgC GAA GAA AGC TGT TCC ACC A 3' | 6 |

TABLE 9-continued

Sequence Listing Table

| DESCRIPTION | SEQ ID NO |
|---|---|
| RBDVMP3' primer for cloning RBDV movement protein gene<br>5' CCC ACG AAG CTT TTA ATA AAC GGA ATG TGA AGG 3' | 7 |
| RBDVMP5' primer for cloning RBDV movement protein gene<br>5' TGC TCT AGA ATG TTT AGC AGA AGT TCC 3' | 8 |
| mutation primer RBDVM1<br>5' GGC CGC TCT AGA AGG TTT TAA AGA AGT TAA TCT ACT CGC AGC TCC C 3' | 9 |
| mutation primer RBDVM2<br>5' GGC CGC TCT AGA ATG TCT ACT CGC AGC TCC CTT G 3' | 10 |
| mutation primer RBDVM3<br>5' CGC TCT AGA ATG TTT AGC AGA AGC AGG AGT GGC TCC 3' | 11 |
| mutation primer RBDVM4<br>5' CTG TGA GGG GGT TCT CTC GAG GAT TAC CTT CCG CC 3' | 12 |
| modified movement protein coding sequence-RBDVM1 (FIG. 5A) | 13 |
| modified movement protein coding sequence-RBDVM2 (FIG. 5B) | 14 |
| modified movement protein coding sequence-RBDVM3 (FIG. 5C) | 15 |
| modified movement protein coding sequence-RBDVM4 (FIG. 5D) | 16 |

It is claimed:

1. An isolated polynucleotide comprising a nucleic acid sequence selected from the group consisting of SEQ ID NO:13, SEQ ID NO:14, SEQ ID NO:15 and SEQ ID NO:16, wherein a transgenic plant that expresses said polynucleotide exhibits greater resistance to RBDV infection than a plant that does not express said polynucleotide.

2. A plant transformation vector comprising the isolated polynucleotide of claim 1.

3. The plant transformation vector of claim 2, wherein the isolated polynucleotide is operably linked to control sequences recognized by a host cell transformed with the vector, and wherein the control sequences include a promoter.

4. A transgenic plant cell comprising the plant transformation vector of claim 3.

5. A transgenic plant comprising the plant cell of claim 4, wherein said plant exhibits enhanced resistance to infection by RBDV relative to a plant of the same species that does not comprise said transgenic plant cell.

6. A method for inducing RBDV resistance in a transgenic raspberry plant, comprising:

(i) introducing into cells of said raspberry plant a plant transformation vector according to claim 2 to produce transformed plant cells; and (ii) growing the transformed plant cells to produce a transgenic raspberry plant, wherein the isolated polynucleotide comprised by said vector is expressed and wherein said transgenic raspberry plant exhibits enhanced resistance to RBDV infection relative to a raspberry plant which has not been so transformed.

7. An RBDV-resistant raspberry plant produced according to the method of claim 6.

* * * * *

SEQUENCE LISTING

```
<160> NUMBER OF SEQ ID NOS: 16

<210> SEQ ID NO 1
<211> LENGTH: 825
<212> TYPE: DNA
<213> ORGANISM: Artificial Sequence
<220> FEATURE:
<223> OTHER INFORMATION: sequence encoding RBDV coat protein

<400> SEQUENCE: 1

atggcgaaga aagctgttcc accaatcgtt aaggctcaat atgagcttta taatcgtaag     60

ttgaacagag ccatcaaggt ttccggcagt cagaagaagc tagacgcttc ttttgtcggg    120

ttcagtgaga gctctaaccc agaaactggg aaacctcacg cggacatgtc tatgtctgct    180

aaggttaagc gcgtcaatac gtggcttaaa aactttgatc gcgaatattg ggataaccag    240

ttcgcatcaa aacccgttcc tagacctgca aaacaggcct tgaagggttc atcctccaaa    300

cctcaacaac gagatgaagg agaggtggtc tttacccgaa aagactccca gaaatccgtt    360

aggactgtgt cctattgggt ttgtactcct gagaagtcga tgaaacctct caaatataag    420

gaggacgaaa acgtcgttga agttaccttc aatgacctca cagctcaaaa ggctggtgac    480

aaattggttt ccattctgtt ggaaatcaat gtggtgggcg gtgccgtcga cgataaaggt    540

cgagtggctg tcctggaaaa ggatgctgcc gtgacggttg attaccttct cggaagcccg    600

tatgaagcca taaatcttgt ttcgggttta aacaagataa attttaggtc catgacggat    660

gtggtagatt ccataccatc gctcttaaat gagcgtaagg tgtgtgtctt ccagaatgac    720

gacagttcgt cgttttacat tcggaaatgg gccaacttcc ttcaggaagt ttcggcagtt    780

ttaccggtag gaaccggtaa atcctccaca atagttctaa cttag                    825


<210> SEQ ID NO 2
<211> LENGTH: 274
<212> TYPE: PRT
<213> ORGANISM: Artificial Sequence
<220> FEATURE:
<223> OTHER INFORMATION: predicted RBDV coat protein sequence

<400> SEQUENCE: 2
```

-continued

```
Met Ala Lys Lys Ala Val Pro Pro Ile Val Lys Ala Gln Tyr Glu Leu
 1               5                  10                  15

Tyr Asn Arg Lys Leu Asn Arg Ala Ile Lys Val Ser Gly Ser Gln Lys
            20                  25                  30

Lys Leu Asp Ala Ser Phe Val Gly Phe Ser Glu Ser Ser Asn Pro Glu
        35                  40                  45

Thr Gly Lys Pro His Ala Asp Met Ser Met Ser Ala Lys Val Lys Arg
    50                  55                  60

Val Asn Thr Trp Leu Lys Asn Phe Asp Arg Glu Tyr Trp Asp Asn Gln
65                  70                  75                  80

Phe Ala Ser Lys Pro Val Pro Arg Pro Ala Lys Gln Ala Leu Lys Gly
                85                  90                  95

Ser Ser Ser Lys Pro Gln Gln Arg Asp Glu Gly Glu Val Val Phe Thr
            100                 105                 110

Arg Lys Asp Ser Gln Lys Ser Val Arg Thr Val Ser Tyr Trp Val Cys
        115                 120                 125

Thr Pro Glu Lys Ser Met Lys Pro Leu Lys Tyr Lys Glu Asp Glu Asn
    130                 135                 140

Val Val Glu Val Thr Phe Asn Asp Leu Thr Ala Gln Lys Ala Gly Asp
145                 150                 155                 160

Lys Leu Val Ser Ile Leu Leu Glu Ile Asn Val Val Gly Gly Ala Val
                165                 170                 175

Asp Asp Lys Gly Arg Val Ala Val Leu Glu Lys Asp Ala Ala Val Thr
            180                 185                 190

Val Asp Tyr Leu Leu Gly Ser Pro Tyr Glu Ala Ile Asn Leu Val Ser
        195                 200                 205

Gly Leu Asn Lys Ile Asn Phe Arg Ser Met Thr Asp Val Val Asp Ser
    210                 215                 220

Ile Pro Ser Leu Leu Asn Glu Arg Lys Val Cys Val Phe Gln Asn Asp
225                 230                 235                 240

Asp Ser Ser Ser Phe Tyr Ile Arg Lys Trp Ala Asn Phe Leu Gln Glu
                245                 250                 255

Val Ser Ala Val Leu Pro Val Gly Thr Gly Lys Ser Ser Thr Ile Val
            260                 265                 270

Leu Thr
```

<210> SEQ ID NO 3
<211> LENGTH: 1077
<212> TYPE: DNA
<213> ORGANISM: Artificial Sequence
<220> FEATURE:
<223> OTHER INFORMATION: sequence encoding RBDV movement protein

<400> SEQUENCE: 3

```
atgtttagca gaagttcctc tactcgcagc tcccttgtgg ggagcaggag tggctccatt     60

tttggagggg gatctgttaa gaagtctagt actgtgaggg ggttctctgc cggtcttgaa    120

agatcgcgag gattaccttc cgccagcgct ggtgaaaacc agatctcgct gccggggctt    180

aggatcccag ttaaggcttc ttcacaaccg ggaaattact accttaagga gagaggtatt    240

gatttgccaa ttgtgcaaca gcagaagttt ctagccgctg acggcaaaga aatgggggag    300

tgttaccttt tggacacttc ccgaactgat ctgttggacg ctgccaaagc agcgttaaac    360

gagtctaatc ttcttgaatt caacaaattt aaggaattta agaagtataa gggaaagaat    420

aatgaattct ctttggttga ggcatcagtt tttgataaac tgatcaggaa ggacgattct    480
```

-continued cccatacacc ttaacaggct tttaatagct gttttacctg ccgtaggaaa aggaacacca 540
ggaaccgcac gaattaaaat tcgtgacgcg cgcctggatg atggttatgg tgagcttttt 600
agttctgaaa atcgtgtgga ctctggctac atttattgta taaatgtagg ttattctgtt 660
cctaagtctg aaatcgatta caaaatcaat attgattttg ccggggtacc catcaaagat 720
ggtaagtccc cgatttgggt caaggctgcc ttctctttag ctggtggccc ccctgtgttc 780
cttgatggaa caatgagctt gggtgctgag attttgcccg actctcataa agagctgttg 840
ggcacctctg ctttgttgtt gaatgaggcg aattctaata ggaagtcgtt ctctggtgat 900
gacggagagc ttagaaggga ttacccttat aagcgttttg aggaaatttc acctttggat 960
tctataagtc aggtcgatac ggccagtcaa gactccgtta atgaggtgaa caccgaaaat 1020
gttcaaaacg gtactggtga ggtgtatttg gcacctcctt cacattccgt ttattaa 1077

<210> SEQ ID NO 4
<211> LENGTH: 358
<212> TYPE: PRT
<213> ORGANISM: Artificial Sequence
<220> FEATURE:
<223> OTHER INFORMATION: predicted RBDV movement protein sequence

<400> SEQUENCE: 4

Met Phe Ser Arg Ser Ser Ser Thr Arg Ser Ser Leu Val Gly Ser Arg
1 5 10 15

Ser Gly Ser Ile Phe Gly Gly Gly Ser Val Lys Lys Ser Ser Thr Val
20 25 30

Arg Gly Phe Ser Ala Gly Leu Glu Arg Ser Arg Gly Leu Pro Ser Ala
35 40 45

Ser Ala Gly Glu Asn Gln Ile Ser Leu Pro Gly Leu Arg Ile Pro Val
50 55 60

Lys Ala Ser Ser Gln Pro Gly Asn Tyr Tyr Leu Lys Glu Arg Gly Ile
65 70 75 80

Asp Leu Pro Ile Val Gln Gln Gln Lys Phe Leu Ala Ala Asp Gly Lys
85 90 95

Glu Met Gly Glu Cys Tyr Leu Leu Asp Thr Ser Arg Thr Asp Leu Leu
100 105 110

Asp Ala Ala Lys Ala Ala Leu Asn Glu Ser Asn Leu Leu Glu Phe Asn
115 120 125

Lys Phe Lys Glu Phe Lys Lys Tyr Lys Gly Lys Asn Asn Glu Phe Ser
130 135 140

Leu Val Glu Ala Ser Val Phe Asp Lys Leu Ile Arg Lys Asp Asp Ser
145 150 155 160

Pro Ile His Leu Asn Arg Leu Leu Ile Ala Val Leu Pro Ala Val Gly
165 170 175

Lys Gly Thr Pro Gly Thr Ala Arg Ile Lys Ile Arg Asp Ala Arg Leu
180 185 190

Asp Asp Gly Tyr Gly Glu Leu Phe Ser Ser Glu Asn Arg Val Asp Ser
195 200 205

Gly Tyr Ile Tyr Cys Ile Asn Val Gly Tyr Ser Val Pro Lys Ser Glu
210 215 220

Ile Asp Tyr Lys Ile Asn Ile Asp Phe Ala Gly Val Pro Ile Lys Asp
225 230 235 240

Gly Lys Ser Pro Ile Trp Val Lys Ala Ala Phe Ser Leu Ala Gly Gly
245 250 255

Pro Pro Val Phe Leu Asp Gly Thr Met Ser Leu Gly Ala Glu Ile Leu

-continued

```
            260                 265                 270

Pro Asp Ser His Lys Glu Leu Leu Gly Thr Ser Ala Leu Leu Leu Asn
        275                 280                 285

Glu Ala Asn Ser Asn Arg Lys Ser Phe Ser Gly Asp Asp Gly Glu Leu
    290                 295                 300

Arg Arg Asp Tyr Pro Tyr Lys Arg Phe Glu Glu Ile Ser Pro Leu Asp
305                 310                 315                 320

Ser Ile Ser Gln Val Asp Thr Ala Ser Gln Asp Ser Val Asn Glu Val
                325                 330                 335

Asn Thr Glu Asn Val Gln Asn Gly Thr Gly Glu Val Tyr Leu Ala Pro
            340                 345                 350

Pro Ser His Ser Val Tyr
        355
```

<210> SEQ ID NO 5
<211> LENGTH: 32
<212> TYPE: DNA
<213> ORGANISM: Artificial Sequence
<220> FEATURE:
<223> OTHER INFORMATION: primer

<400> SEQUENCE: 5
cctctagact aagttagaac tattgtggag ga 32

<210> SEQ ID NO 6
<211> LENGTH: 34
<212> TYPE: DNA
<213> ORGANISM: Artificial Sequence
<220> FEATURE:
<223> OTHER INFORMATION: primer

<400> SEQUENCE: 6
cctctagacc atggcgaaga aagctgttcc acca 34

<210> SEQ ID NO 7
<211> LENGTH: 33
<212> TYPE: DNA
<213> ORGANISM: Artificial Sequence
<220> FEATURE:
<223> OTHER INFORMATION: primer

<400> SEQUENCE: 7
cccacgaagc ttttaataaa cggaatgtga agg 33

<210> SEQ ID NO 8
<211> LENGTH: 27
<212> TYPE: DNA
<213> ORGANISM: Artificial Sequence
<220> FEATURE:
<223> OTHER INFORMATION: primer

<400> SEQUENCE: 8
tgctctagaa tgtttagcag aagttcc 27

<210> SEQ ID NO 9
<211> LENGTH: 46
<212> TYPE: DNA
<213> ORGANISM: Artificial Sequence
<220> FEATURE:
<223> OTHER INFORMATION: primer

<400> SEQUENCE: 9
ggccgctcta gaaggtttta aagaagttaa tctactcgca gctccc 46

-continued

<210> SEQ ID NO 10
<211> LENGTH: 34
<212> TYPE: DNA
<213> ORGANISM: Artificial Sequence
<220> FEATURE:
<223> OTHER INFORMATION: primer

<400> SEQUENCE: 10
ggccgctcta gaatgtctac tcgcagctcc cttg 34

<210> SEQ ID NO 11
<211> LENGTH: 36
<212> TYPE: DNA
<213> ORGANISM: Artificial Sequence
<220> FEATURE:
<223> OTHER INFORMATION: primer

<400> SEQUENCE: 11
cgctctagaa tgtttagcag aagcaggagt ggctcc 36

<210> SEQ ID NO 12
<211> LENGTH: 35
<212> TYPE: DNA
<213> ORGANISM: Artificial Sequence
<220> FEATURE:
<223> OTHER INFORMATION: primer

<400> SEQUENCE: 12
ctgtgagggg gttctctcga ggattacctt ccgcc 35

<210> SEQ ID NO 13
<211> LENGTH: 1077
<212> TYPE: DNA
<213> ORGANISM: Artificial Sequence
<220> FEATURE:
<223> OTHER INFORMATION: modified movement protein coding sequence
RBDVM1

<400> SEQUENCE: 13
aggttttaaa gaagttaatc tactcgcagc tcccttgtgg ggagcaggag tggctccatt 60
tttggagggg gatctgttaa gaagtctagt actgtgaggg ggttctctgc cggtcttgaa 120
agatcgcgag gattaccttc cgccagcgct ggtgaaaacc agatctcgct gccggggctt 180
aggatcccag ttaaggcttc ttcacaaccg ggaaattact accttaagga gagaggtatt 240
gatttgccaa ttgtgcaaca gcagaagttt ctagccgctg acggcaaaga aatgggggag 300
tgttaccttt tggacacttc ccgaactgat ctgttggacg ctgccaaagc agcgttaaac 360
gagtctaatc ttcttgaatt caacaaattt aaggaattta agaagtataa gggaaagaat 420
aatgaattct ctttggttga ggcatcagtt tttgataaac tgatcaggaa ggacgattct 480
cccatacacc ttaacaggct tttaatagct gttttacctg ccgtaggaaa aggaacacca 540
ggaaccgcac gaattaaaat tcgtgacgcg cgcctggatg atggttatgg tgagcttttt 600
agttctgaaa atcgtgtgga ctctggctac atttattgta taaatgtagg ttattctgtt 660
cctaagtctg aaatcgatta caaaatcaat attgattttg ccggggtacc catcaaagat 720
ggtaagtccc cgatttgggt caaggctgcc ttctctttag ctggtggccc ccctgtgttc 780
cttgatggaa caatgagctt gggtgctgag attttgcccg actctcataa agagctgttg 840
ggcacctctg ctttgttgtt gaatgaggcg aattctaata ggaagtcgtt ctctggtgat 900
gacggagagc ttagaaggga ttacccttat aagcgttttg aggaaatttc acctttggat 960

-continued

```
tctataagtc aggtcgatac ggccagtcaa gactccgtta atgaggtgaa caccgaaaat   1020

gttcaaaacg gtactggtga ggtgtatttg gcacctcctt cacattccgt ttattaa      1077


<210> SEQ ID NO 14
<211> LENGTH: 1062
<212> TYPE: DNA
<213> ORGANISM: Artificial Sequence
<220> FEATURE:
<223> OTHER INFORMATION: modified movement protein coding sequence
      RBDVM2

<400> SEQUENCE: 14

atgtctactc gcagctccct tgtggggagc aggagtggct ccatttttgg agggggatct     60

gttaagaagt ctagtactgt gagggggttc tctgccggtc ttgaaagatc gcgaggatta    120

ccttccgcca gcgctggtga aaaccagatc tcgctgccgg ggcttaggat cccagttaag    180

gcttcttcac aaccgggaaa ttactacctt aaggagagag gtattgattt gccaattgtg    240

caacagcaga agtttctagc cgctgacggc aaagaaatgg gggagtgtta ccttttggac    300

acttcccgaa ctgatctgtt ggacgctgcc aaagcagcgt taaacgagtc taatcttctt    360

gaattcaaca aatttaagga atttaagaag tataagggaa agaataatga attctctttg    420

gttgaggcat cagtttttga taaactgatc aggaaggacg attctcccat acaccttaac    480

aggcttttaa tagctgtttt acctgccgta ggaaaaggaa caccaggaac cgcacgaatt    540

aaaattcgtg acgcgcgcct ggatgatggt tatggtgagc tttttagttc tgaaaatcgt    600

gtggactctg gctacattta ttgtataaat gtaggttatt ctgttcctaa gtctgaaatc    660

gattacaaaa tcaatattga ttttgccggg gtacccatca aagatggtaa gtccccgatt    720

tgggtcaagg ctgccttctc tttagctggt ggccccccctg tgttccttga tggaacaatg    780

agcttgggtg ctgagatttt gcccgactct cataaagagc tgttgggcac ctctgctttg    840

ttgttgaatg aggcgaattc taataggaag tcgttctctg gtgatgacgg agagcttaga    900

agggattacc cttataagcg ttttgaggaa atttcacctt tggattctat aagtcaggtc    960

gatacggcca gtcaagactc cgttaatgag gtgaacaccg aaaatgttca aaacggtact   1020

ggtgaggtgt atttggcacc tccttcacat tccgtttatt aa                      1062


<210> SEQ ID NO 15
<211> LENGTH: 1047
<212> TYPE: DNA
<213> ORGANISM: Artificial Sequence
<220> FEATURE:
<223> OTHER INFORMATION: modified movement protein coding sequence
      RBDVM3

<400> SEQUENCE: 15

atgtttagca gaagcaggag tggctccatt tttggagggg gatctgttaa gaagtctagt     60

actgtgaggg ggttctctgc cggtcttgaa agatcgcgag gattaccttc cgccagcgct    120

ggtgaaaacc agatctcgct gccggggctt aggatcccag ttaaggcttc ttcacaaccg    180

ggaaattact accttaagga gagaggtatt gatttgccaa ttgtgcaaca gcagaagttt    240

ctagccgctg acggcaaaga aatgggggag tgttaccttt tggacacttc ccgaactgat    300

ctgttggacg ctgccaaagc agcgttaaac gagtctaatc ttcttgaatt caacaaattt    360

aaggaattta agaagtataa gggaaagaat aatgaattct ctttggttga ggcatcagtt    420

tttgataaac tgatcaggaa ggacgattct cccatacacc ttaacaggct tttaatagct    480
```

-continued

```
gttttacctg ccgtaggaaa aggaacacca ggaaccgcac gaattaaaat tcgtgacgcg    540

cgcctggatg atggttatgg tgagcttttt agttctgaaa atcgtgtgga ctctggctac    600

atttattgta taaatgtagg ttattctgtt cctaagtctg aaatcgatta caaaatcaat    660

attgattttg ccggggtacc catcaaagat ggtaagtccc cgatttgggt caaggctgcc    720

ttctctttag ctggtggccc ccctgtgttc cttgatggaa caatgagctt gggtgctgag    780

attttgcccg actctcataa agagctgttg ggcacctctg ctttgttgtt gaatgaggcg    840

aattctaata ggaagtcgtt ctctggtgat gacggagagc ttagaaggga ttacccttat    900

aagcgttttg aggaaatttc acctttggat tctataagtc aggtcgatac ggccagtcaa    960

gactccgtta atgaggtgaa caccgaaaat gttcaaaacg gtactggtga ggtgtatttg   1020

gcacctcctt cacattccgt ttattaa                                       1047


<210> SEQ ID NO 16
<211> LENGTH: 1059
<212> TYPE: DNA
<213> ORGANISM: Artificial Sequence
<220> FEATURE:
<223> OTHER INFORMATION: modified movement protein coding sequence
      RBDVM4

<400> SEQUENCE: 16

atgtttagca gaagttcctc tactcgcagc tcccttgtgg ggagcaggag tggctccatt     60

tttggagggg gatctgttaa gaagtctagt actgtgaggg ggttctctcg aggattacct    120

tccgccagcg ctggtgaaaa ccagatctcg ctgccggggc ttaggatccc agttaaggct    180

tcttcacaac cgggaaatta ctaccttaag gagagaggta ttgatttgcc aattgtgcaa    240

cagcagaagt ttctagccgc tgacggcaaa gaaatggggg agtgttacct tttggacact    300

tcccgaactg atctgttgga cgctgccaaa gcagcgttaa acgagtctaa tcttcttgaa    360

ttcaacaaat ttaaggaatt taagaagtat aagggaaaga ataatgaatt ctctttggtt    420

gaggcatcag tttttgataa actgatcagg aaggacgatt ctcccataca ccttaacagg    480

cttttaatag ctgttttacc tgccgtagga aaaggaacac caggaaccgc acgaattaaa    540

attcgtgacg cgcgcctgga tgatggttat ggtgagcttt ttagttctga aaatcgtgtg    600

gactctggct acatttattg tataaatgta ggttattctg ttcctaagtc tgaaatcgat    660

tacaaaatca atattgattt tgccggggta cccatcaaag atggtaagtc cccgatttgg    720

gtcaaggctg ccttctcttt agctggtggc ccccctgtgt tccttgatgg aacaatgagc    780

ttgggtgctg agattttgcc cgactctcat aaagagctgt tgggcacctc tgctttgttg    840

ttgaatgagg cgaattctaa taggaagtcg ttctctggtg atgacggaga gcttagaagg    900

gattaccctt ataagcgttt tgaggaaatt tcacctttgg attctataag tcaggtcgat    960

acggccagtc aagactccgt taatgaggtg aacaccgaaa atgttcaaaa cggtactggt   1020

gaggtgtatt tggcacctcc ttcacattcc gtttattaa                          1059
```